(12) United States Patent
Horibe et al.

(10) Patent No.: US 12,127,732 B2
(45) Date of Patent: Oct. 29, 2024

(54) DISTAL END UNIT FOR ENDOSCOPE AND ENDOSCOPE

(71) Applicant: OLYMPUS CORPORATION, Tokyo (JP)

(72) Inventors: Takuro Horibe, Funabashi (JP); Hiroyuki Motohara, Hachioji (JP); Kenjiro Kanno, Komagane (JP)

(73) Assignee: OLYMPUS CORPORATION, Tokyo (JP)

( * ) Notice: Subject to any disclaimer, the term of this patent is extended or adjusted under 35 U.S.C. 154(b) by 528 days.

(21) Appl. No.: 17/495,204

(22) Filed: Oct. 6, 2021

(65) Prior Publication Data
US 2022/0022733 A1    Jan. 27, 2022

Related U.S. Application Data

(63) Continuation of application No. PCT/JP2019/017182, filed on Apr. 23, 2019.

(51) Int. Cl.
*A61B 1/05*  (2006.01)
*A61B 1/00*  (2006.01)

(52) U.S. Cl.
CPC .......... *A61B 1/051* (2013.01); *A61B 1/00018* (2013.01); *A61B 1/00096* (2013.01); *A61B 1/05* (2013.01)

(58) Field of Classification Search
CPC ............ A61B 1/00018; A61B 1/00096; A61B 1/00149; A61B 1/05; A61B 1/051
See application file for complete search history.

(56) References Cited

U.S. PATENT DOCUMENTS

2002/0040179 A1*  4/2002  Takahashi ................ A61B 1/05
                                                              600/129
2010/0201794 A1*  8/2010  Kido ........................ A61B 1/05
                                                              348/373
(Continued)

FOREIGN PATENT DOCUMENTS

CN        103491845 A    1/2014
CN        105278232 A    1/2016
(Continued)

OTHER PUBLICATIONS

International Search Report dated Jul. 16, 2019 received in PCT/JP2019/017182.

*Primary Examiner* — Aaron B Fairchild
(74) *Attorney, Agent, or Firm* — Scully, Scott, Murphy & Presser, P.C.

(57) ABSTRACT

A distal end unit for endoscope is provided in a distal end portion of an insertion portion and includes: an electronic module including an optical system and an electrode; a substrate including a connection portion electrically connected to the electrode of the electronic module, and including a connection land on which an electronic component is mounted; a holding member holding the electronic module and the substrate connected to the electrode; and a distal end frame body made of resin, on which the electronic module, the substrate and the holding member are integrally mounted via insert molding by loading the holding member holding the electronic module and the substrate in a mold such that an entrance surface of the optical system is exposed at an outer surface of the distal end frame body and the connection portion extends to a proximal end side.

18 Claims, 16 Drawing Sheets

(56) References Cited

U.S. PATENT DOCUMENTS

| | | |
|---|---|---|
| 2013/0303853 A1 | 11/2013 | Takahashi et al. |
| 2015/0369926 A1 | 12/2015 | Ichimura et al. |
| 2018/0235445 A1 | 8/2018 | Sasamura et al. |

FOREIGN PATENT DOCUMENTS

| | | |
|---|---|---|
| CN | 106817891 A | 6/2017 |
| JP | 2003-190085 A | 7/2003 |
| JP | 2004-305770 A | 11/2004 |
| JP | 2005-013708 A | 1/2005 |
| JP | 2006-320543 A | 11/2006 |
| JP | 2009-125528 A | 6/2009 |
| JP | 2010-091986 A | 4/2010 |
| JP | 2012-075658 A | 4/2012 |
| JP | 6008266 B2 | 10/2016 |
| WO | 2008/102575 A1 | 8/2008 |
| WO | 2011/092901 A1 | 8/2011 |
| WO | 2017/203594 A1 | 11/2017 |

\* cited by examiner

DISTAL END UNIT FOR ENDOSCOPE AND ENDOSCOPE

CROSS REFERENCE TO RELATED APPLICATION

This application is a continuation application of PCT/JP2019/017182 filed on Apr. 23, 2019, the entire contents of which are incorporated herein by this reference.

BACKGROUND OF THE INVENTION

1. Field of the Invention

The present invention relates to a distal end unit in which an electronic module is mounted, the distal end unit being provided in a distal end of an insertion portion of an endoscope, and an endoscope.

2. Description of the Related Art

As is well known, endoscopes have been widely used for, e.g., observation or treatment of an inside of a living body (an inside of a body cavity) or, e.g., inspection or repair of the inside of industrial plant equipment. Such an endoscope includes an insertion portion to be inserted into a flexed tubular passage. As such an endoscope, an endoscope having a configuration in which e.g., an image pickup apparatus, which is an electronic module, is provided in a distal end portion of an insertion portion has been known.

An example of a conventional image pickup apparatus as an electronic module is disclosed in International Publication WO 2008-102575, although the image pickup apparatus is not an image pickup apparatus for endoscope. The conventional image pickup apparatus employs a technique in which a conductive member is insert-molded inside a resin plate to allow a wiring from an image pickup device and a wiring of a substrate to be electrically connected via the conductive member.

This conventional image pickup apparatus has a structure in which a resin plate with a conductive member insert-molded is attached to a rear surface of an image pickup device and terminals exposed at a surface of the resin plate are electrically connected to terminals of another member such as a substrate.

SUMMARY OF THE INVENTION

A distal end unit for endoscope according to an aspect of the present invention is provided in a distal end portion of an insertion portion. The distal end unit includes: an electronic module including an optical system and an electrode; a substrate including a connection portion electrically connected to the electrode of the electronic module, and including a connection land on which an electronic component is mounted; a holding member holding the electronic module and the substrate connected to the electrode; and a distal end frame body made of resin on which the electronic module, the substrate and the holding member are integrally mounted via insert molding by loading the holding member holding the electronic module and the substrate in a mold such that an entrance surface of the optical system is exposed at an outer surface of the distal end frame body and the connection portion extends to a proximal end side.

An endoscope according to an aspect of the present invention includes a distal end unit provided in a distal end portion of an insertion portion. The distal end unit includes: an electronic module including an optical system and an electrode; a substrate including a connection portion electrically connected to the electrode of the electronic module, and including a connection land on which an electronic component is mounted; a holding member holding the electronic module and the substrate connected to the electrode; and a distal end frame body made of resin on which the electronic module, the substrate and the holding member are integrally mounted via insert molding by loading the holding member holding the electronic module and the substrate in a mold such that an entrance surface of the optical system is exposed at an outer surface of the distal end frame body and the connection portion extends to a proximal end side.

DETAILED DESCRIPTION OF THE PREFERRED EMBODIMENTS

Figure 1:
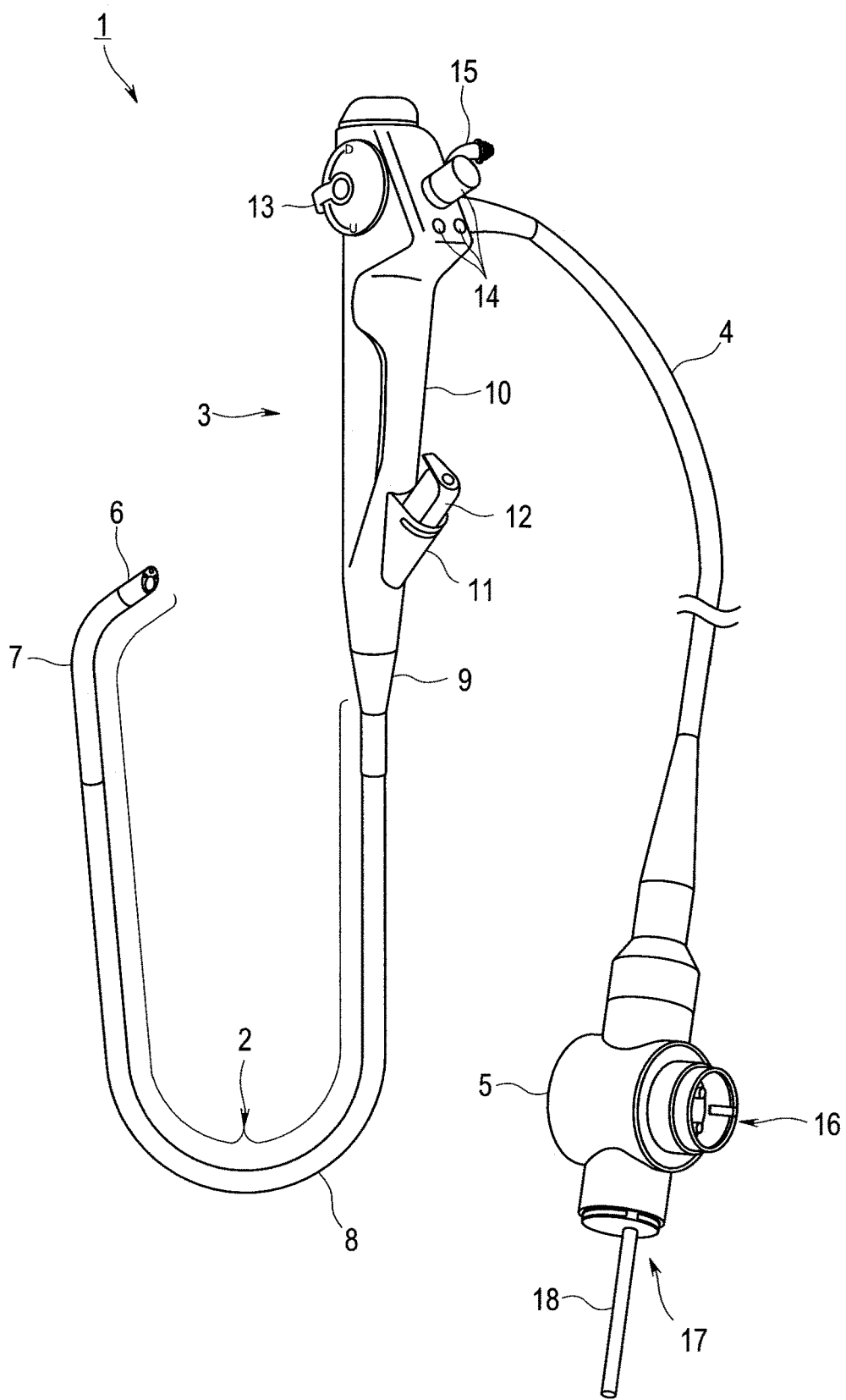
FIG. 1 is a diagram illustrating an outer appearance of an endoscope according to an embodiment of the present invention.

An embodiment of a distal end unit for endoscope and an endoscope according to the present invention will be described below. In the below description, it should be noted that diagrams based on the embodiment and modifications are schematic ones and, e.g., a relationship between a thickness and a width of each part and ratios in thickness among the respective parts are different from actual ones. Parts that are different in dimensional relationship and/or ratio depending on the drawings may be included in the drawings.

Also, an endoscope in the below description is an example of an endoscope including a small-diameter insertion portion such as a bronchoscope or an urological endoscope; however, the present invention is not limited to this example and is applicable also to what is called a flexible scope including a flexible insertion portion for insertion into a digestive organ in a upper part or a lower part of a living body or what is called a rigid endoscope including a rigid insertion portion, which is used for surgery.

An endoscope according to an embodiment of the present invention will be described below with reference to the drawings.

As illustrated in FIG. 1, an endoscope 1, which is an electronic endoscope of the present embodiment, mainly includes, e.g., an insertion portion 2 formed in an elongated tubular shape, an operation portion 3 provided in such a manner as to be continuous with a proximal end of the insertion portion 2, a universal cord 4, Which is an endoscope cable provided in such a manner as to extend from the operation portion 3, and an endoscope connector 5 disposed at a distal end of the universal cord 4.

The insertion portion 2 is a flexible tubular member formed by a distal end portion 6, a bending portion 7 and a flexible tube portion 8 being continuously provided in the order mentioned from the distal end side. From among these portions, in the distal end portion 6, e.g., a later-described image pickup unit 30, which is an image pickup apparatus, and illumination means are housed and arranged.

The bending portion 7 is a mechanism part configured to be capable of actively bending in two directions (up-down)

of the insertion portion 2 via an operation of rotating a bending lever 13 from among operation members of the operation portion 3.

The bending portion 7 is not limited to a type of bending portion that actively bends in two, up and down, directions, and may be a type of bending portion that can bend in four directions including left and right directions in addition to the up and down directions (all directions, i.e., up-down/left-right, around an axis via up, down, left and right operations), a type of bending portion that can bend only one, up, direction or a type of bending portion that has no mechanism actively bending via the bending lever 13 and that simply passively bends.

The flexible tube portion 8 is a tubular member having flexibility so that the tubular member can be passively flexed. Inside the flexible tube portion 8, in addition to a later-described treatment instrument insertion channel, e.g., an image pickup cable extending from the image pickup apparatus incorporated in the distal end portion 6 and further extending from the operation portion 3 to the inside of the universal cord 4, and a light guide bundle configured to guide illuminating light from a light source apparatus and make the illuminating light exit from the distal end portion 6 (none of which are illustrated here) are inserted.

The operation portion 3 includes: a bent preventing portion 9 provided on the distal end side, the bent preventing portion 9 covering a proximal end of the flexible tube portion 8 and being connected to the flexible tube portion 8; a grasping portion 10 provided in such a manner as to be continuous with the bent preventing portion 9, the grasping portion 10 being configured to be grasped by a hand of a user when the user uses the endoscope 1; operation means for operating various endoscope functions, the operation means being provided at an outer surface of the grasping portion 10; a treatment instrument insertion portion 11; and a suction valve 15.

Examples of the operation means provided at the operation portion 3 include, e.g., the bending lever 13 for performing an operation of bending the bending portion 7 and a plurality of operation members 14 for performing air/water feeding operation, suction operation or respective operations for, e.g., image pickup means or the illumination means.

The treatment instrument insertion portion 11 is a component portion including a treatment instrument insertion opening that allows insertion of any of various treatment instrument (not illustrated) communicating with the treatment instrument insertion channel (not illustrated) via a branching member inside the operation portion 3.

In the treatment instrument insertion portion 11, a forceps plug 12, which is a lid member for opening/closing the treatment instrument insertion opening and is configured in such a manner as to be detachably (replaceably) attached to the treatment instrument insertion portion 11 is disposed. The treatment instrument insertion channel also communicates with the suction valve 15 via a branching member inside the operation portion 3.

The universal cord 4 is a composite cable extending from the distal end portion 6 of the insertion portion 2 to the operation portion 3 through an inside of the insertion portion 2 and, e.g., a signal cable bundle and a light guide bundle configured to convey illuminating light from the light source apparatus (not illustrated.) being inserted in the universal cord 4.

The endoscope connector 5 includes, e.g., an electric connector portion 16 at a side surface portion, a signal cable for connection with a video processor (not illustrated), which is an external apparatus, being connected to the electric connector portion 16, and a light source connector portion 17 including a light source connection plug 18 to which the later-described light guide bundle for connection with the light source apparatus, which is an external device, and an electric cable (not illustrated) are connected.

Here, a configuration of a distal end part of the insertion portion 2 of the endoscope 1 of the present embodiment will be described below with reference to FIGS. 2 to 4. In the below description, description of well-known components of the insertion portion 2 are omitted.

Figure 2:
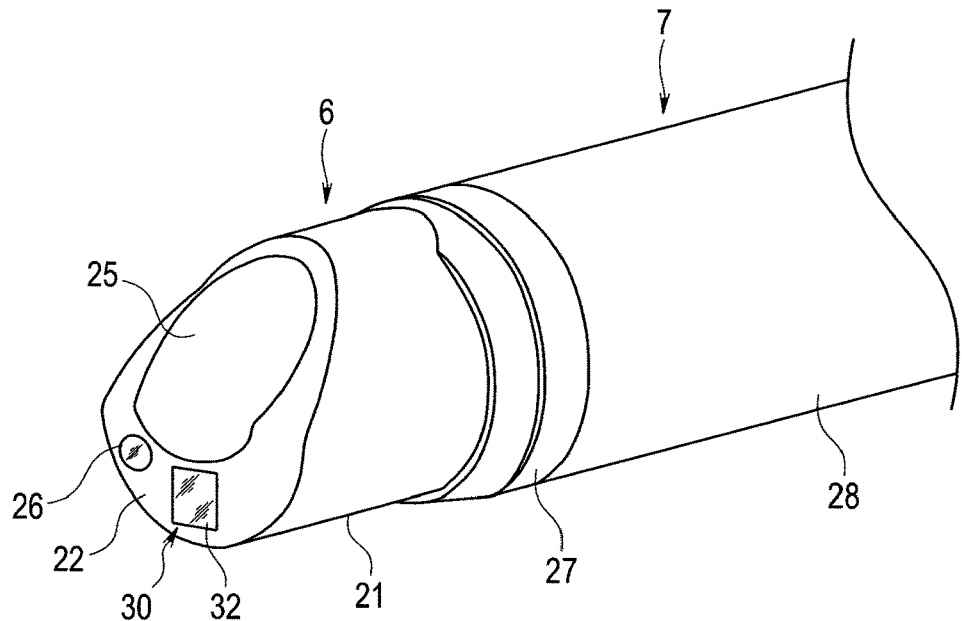
FIG. 2 is a perspective view illustrating a configuration of a distal end part of an insertion portion according to the embodiment of the present invention.
Figure 3:
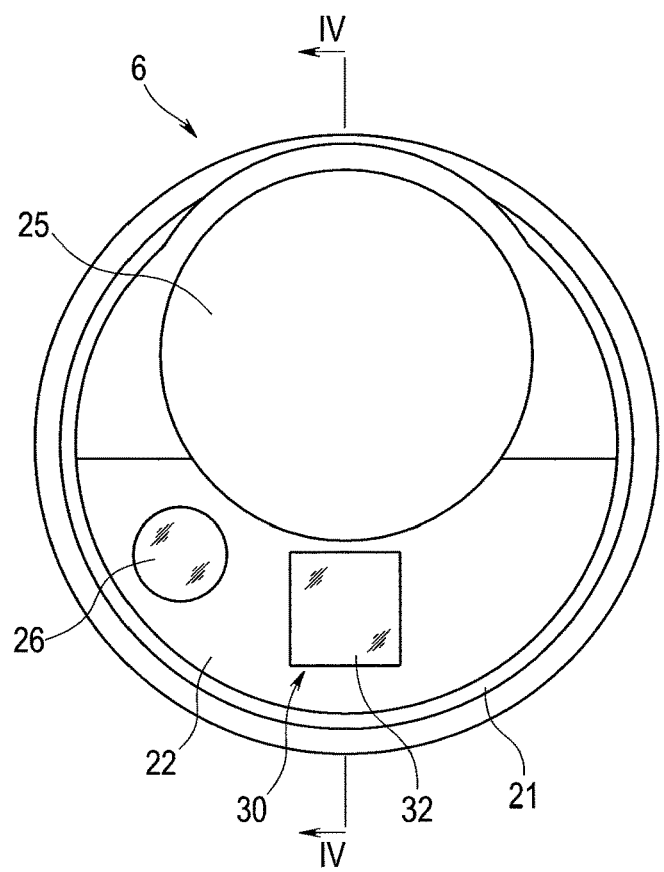
FIG. 3 is a front view illustrating a configuration of a distal end portion of the insertion portion according to the embodiment of the present invention.

As illustrated in FIGS. 2 and 3, the distal end portion 6 of the insertion portion 2 includes a distal end frame body 21 having a bullet-like shape and configuring a distal end frame made of resin. In the distal end frame body 21, an entrance surface 32 of an optical system 31 provided in the image pickup unit 30, the entrance surface 32 being a rectangular observation window here and allowing entry of observation light on a distal end surface 22, and one illuminating optical system 26, which is a substantially circular illumination window here, are provided. Also, in the distal end frame body 21, an opening portion of a channel 25 configured to guide insertion/removal of, e.g., a treatment instrument is provided. The number of illuminating optical systems 26 is not limited to one but may be two or more.

An outer circumferential part of a proximal end of the distal end frame body 21 is covered by a distal end part of a bending rubber 28, which forms an outer coating of the bending portion 7. A winding bonding portion 27 is provided on an outer circumference of the distal end part of the bending rubber 28, and the bending rubber 28 is fixedly attached to the outer circumferential part of the proximal end of the distal end frame body 21.

Figure 4:
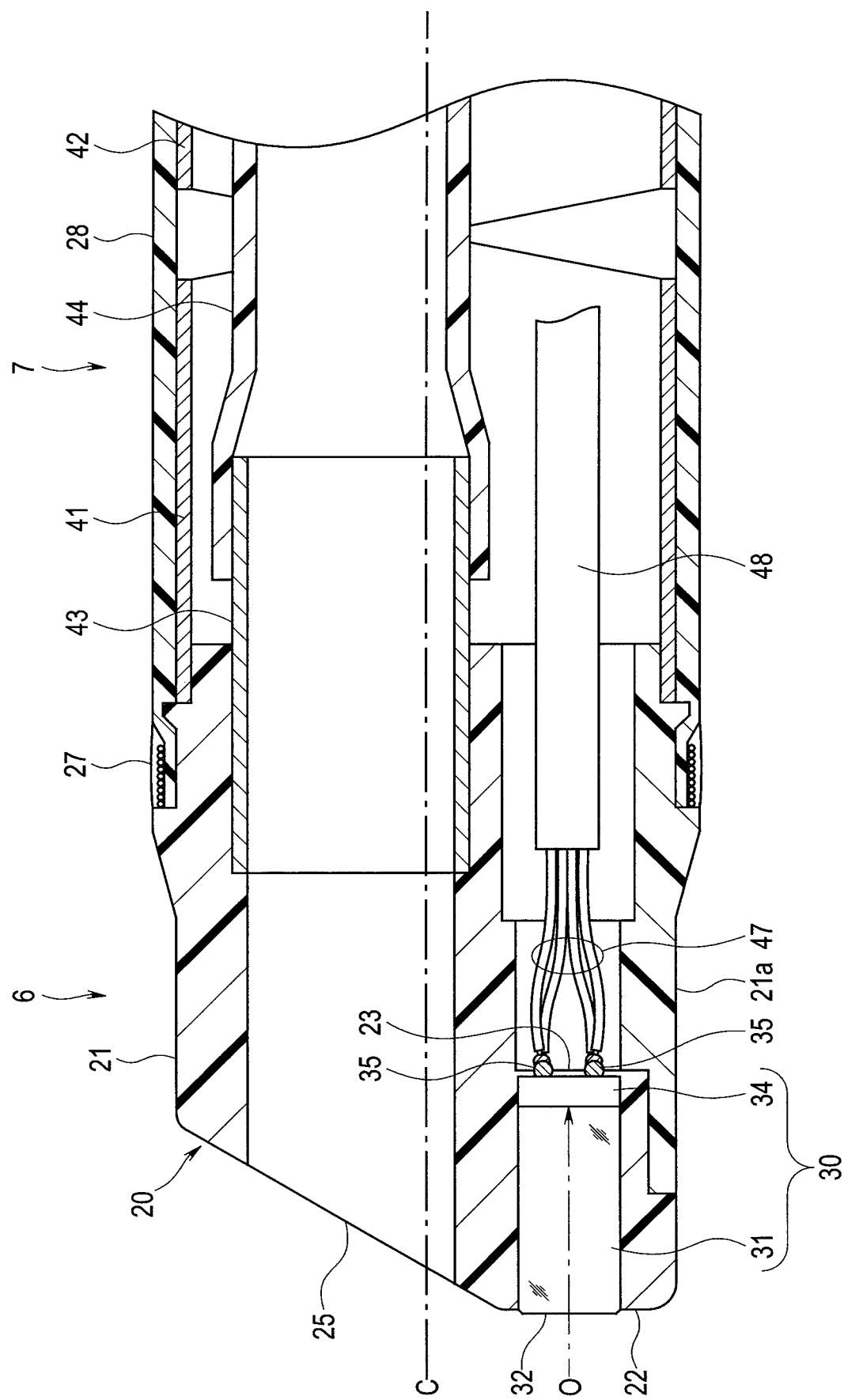
FIG. 4 is a cross-sectional view illustrating a configuration of the distal end part of the insertion portion along line IV-IV in FIG. 3 according to the embodiment of the present invention.

As illustrated in FIG. 4, the image pickup unit 30 is provided inside the distal end frame body 21 of the distal end portion 6. A distal end unit 20 of the endoscope 1 of the present embodiment is configured by the distal end frame body 21 and the image pickup unit 30 integrally insert-molded in the distal end frame body 21.

The present embodiment will be described employing the image pickup unit 30, which is an image pickup apparatus, as an example of the electronic module. Here, the electronic module includes a configuration such as an optical system such as a lens, an image sensor, an optical system and an image sensor, an image sensor and a substrate, an optical system, an image sensor and a cable, an optical system, an image sensor and a holding member, an optical system, an image sensor, a substrate and a holding member, an optical system, an image sensor, a cable and a holding member, or an optical system, an image sensor, a substrate, a cable and a holding member.

The distal end frame body 21 here is configured by two members and has a configuration in which a cover body 21a is provided via bonding and fitting after signal wires 47 of the image pickup cable 48 are electrically connected to a plurality of electrodes 35, which are electric terminals of the image pickup unit 30, respectively.

Although the distal end frame body 21 includes two members including the cover body 21a in order to make it easy to connect the signal wires 47 of the image pickup cable 48 to the plurality of electrodes 35 of the image pickup unit 30 via, e.g., soldering, the distal end frame body 21 may have a configuration simply molded as a single member.

Also, the image pickup unit 30 has a configuration obtained by the image pickup unit 30 being loaded in a non-illustrated mold and integrally molded (insert-molded)

in the distal end frame body 21 made of resin. The configuration of the image pickup unit 30 will be described in detail later.

A distalmost first bending piece 41 provided inside the bending portion 7 is fitted on a proximal end part of the distal end frame body 21 of the distal end portion 6. A second bending piece 42 is turnably joined to a proximal end of the distalmost bending piece 41 and a plurality of bending pieces are turnably provided in a continuous manner inside the bending portion 7.

The plurality of bending pieces including the first bending piece 41 and the second bending piece 42 are covered by the bending rubber 28. The bending portion 7 actively bends in the two, up and down, directions by the plurality of bending pieces including the first bending piece 41 and the second bending piece 42 respectively turning as a result of non-illustrated two bending operation wires being pulled/loosened in response to an operation of the bending lever 13.

A tube connecting pipe 43 made of metal is fitted in a proximal end part of the channel 25 in the distal end frame body 21. A distal end of a channel tube 44, which serves as the treatment instrument insertion channel, is connected to a proximal end of the tube connecting pipe 43.

The above metal tube connecting pipe 43, etc., may be integrally formed in the distal end frame body 21 via insert molding.

Insert molding of the metal tube connecting pipe 43, etc., enables enhancement in rigidity of the proximal end part of the distal end frame body 21 and reduction in thickness and outer diameter of the distal end frame body 21.

Consequently, it is possible to downsize the distal end portion 6 and the bending portion 7 of the endoscope. Furthermore, the need for a step of assembling the tube connecting pipe 43 is eliminated, and as a result, man-hour for assembly is reduced, which leads to cost reduction.

Here, the configuration of the image pickup unit 30 in the present embodiment will be described below with reference to FIGS. 5 and 6.

Figure 5:
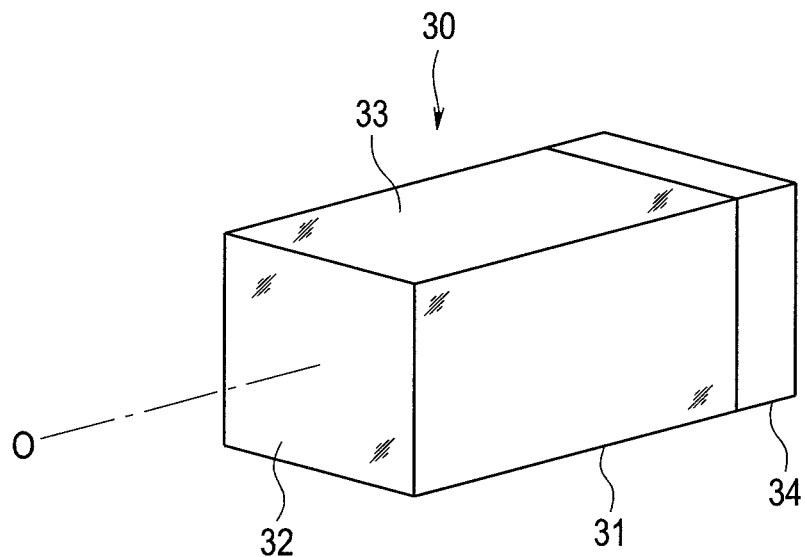
FIG. 5 is a perspective view of an image pickup unit from a front side according to the embodiment of the present invention.
Figure 6:
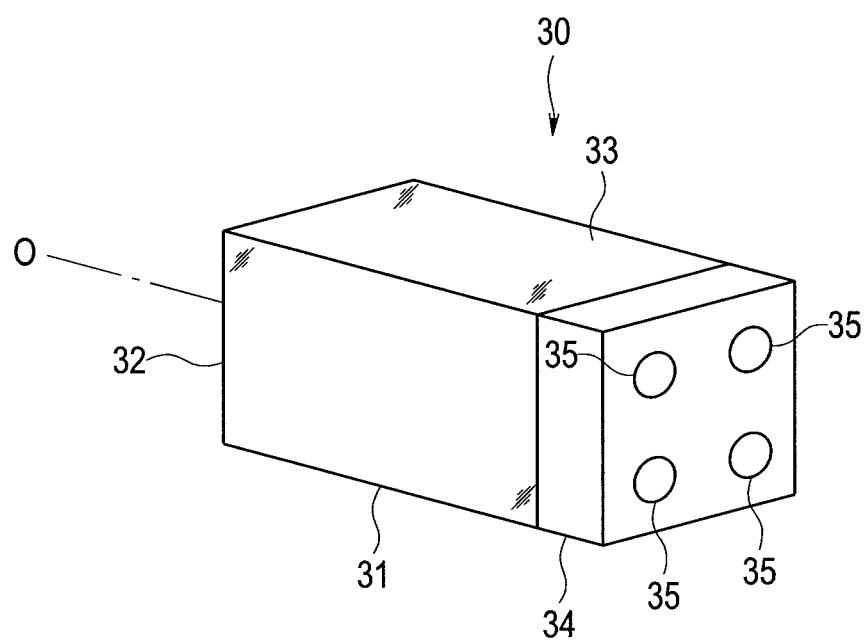
FIG. 6 is a perspective view of the image pickup unit from a back side according to the embodiment of the present invention.

The image pickup unit 30 illustrated in FIGS. 5 and 6 includes the optical system 31 formed of a stack body fabricated using a wafer-level optics technique. The optical system 31 includes at least one lens and forms a subject image on a light-receiving surface of the image sensor 34. The image sensor 34 including an image pickup device, which is an electronic component such as a CCD or a CMOS, is provided in such a manner as to be continuous with the optical system 31 along an image pickup optical axis O, the image sensor 34 being attached to the optical system 31, forming an image pickup package having a rectangular block shape.

The optical system 31 is manufactured by, for example, fabricating a plurality of lens wafers each obtained by a lens being formed on a base material such as a glass substrate, and stacking and dicing these lens wafers.

A surface of the optical system 31 provided on a subject side of the image pickup unit 30 is the entrance surface (distal end surface of the image pickup unit 30) 32 from which light from a subject enters, but side surfaces (side surfaces of the image pickup unit 30) 33 except the entrance surface 32 need to be shielded from light. As a result of the image pickup unit 30 being integrally insert-molded in the distal end frame body 21, the side surfaces 33 of the optical system 31 except the entrance surface 32 are shielded from light.

Also, if the optical system 31 is powered by the entrance surface or an exit surface of the optical system 31 being curved, the optical system 31 can be regarded as an optical lens (convex lens or a concave lens). In this case, the optical system 31 configures a lens necessary for forming a subject image on the light-receiving surface of the image sensor 34, which is an image pickup device.

The electrodes 35, which are a plurality of, here, four solder balls, are provided on a back surface of the image sensor 34. Note that the electrodes 35 are not limited to solder balls but may be a lead frame or terminals having, e.g., a pin shape. Also, the image pickup unit 30 may have a configuration in which a plurality of objective optical systems are held by a lens holding frame.

Figure 7:
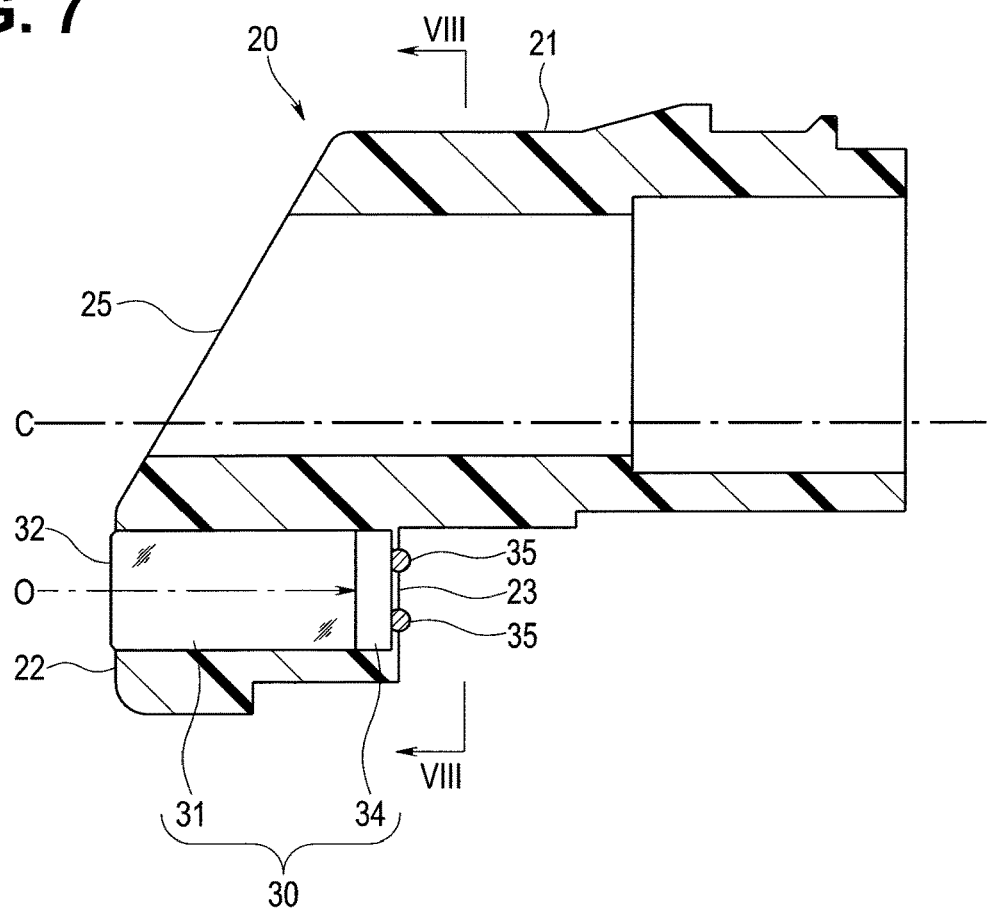
FIG. 7 is a cross-sectional view illustrating a configuration of a distal end unit according to the embodiment of the present invention.
Figure 8:
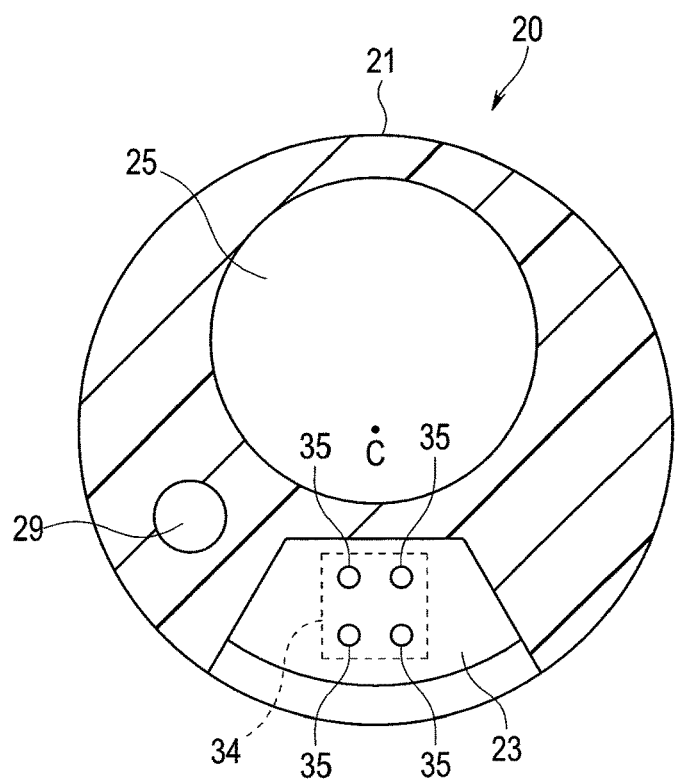
FIG. 8 is a cross-sectional view illustrating a configuration of the distal end unit along line VIII-VIII in FIG. 7 according to the embodiment of the present invention.

As illustrated in FIGS. 7 and 8, the image pickup unit 30 is mounted in the distal end frame body 21 by being formed integrally with the distal end frame body 21 via insert molding in such a manner that a longitudinal axis C of the distal end frame body 21 and the image pickup optical axis O of the optical system 31 are substantially parallel to each other.

In this case, the image pickup unit 30 is mounted in the distal end frame body 21 in such a manner that: the entrance surface 32 of the optical system 31, from which light along the image pickup optical axis O enters, is exposed at the distal end surface 22, which is an outer surface of the distal end frame body 21; and the electrodes 35 of the image sensor 34 at least partly project from one surface 23 on the proximal end side of the distal end frame body 21 inside the distal end portion 6 and are thus exposed.

In other words, the distal end frame body 21 is molded using resin integrally with the image pickup unit 30 loaded in a mold, in such a manner that: the entire entrance surface 32 of the optical system 31 of the image pickup unit 30 or at least an area of the entrance surface 32, where light necessary for forming an optical image on an effective image pickup area of the image sensor 34 enters, is exposed at the outer surface; and the electrodes 35 of the image sensor 34 at least partly project from the one surface 23 on the proximal end side of the distal end frame body 21, the one surface 23 being located inside the distal end portion 6, and are thus exposed.

The optical system 31 of the image pickup unit 30 is provided in such a manner as to slightly project toward the subject side, which is the distal end insertion portion side, relative to the distal end surface 22, which is an outer surface of the distal end frame body 21. Consequently, a surface of the optical system 31 (entrance surface that lets in light from a subject) projects from the distal end surface 22. As a result, a structure in which dirt is not easily accumulated is provided, enabling enhancement in cleaning and sterilization capability and reduction in risk of cross-infection of a patient.

Where, e.g., stray light or a flare is generated because of the side surfaces 33 being partly exposed as a result of the optical system 31 being made to slightly project, exposed parts of the side surfaces 33 may be shielded from light by being covered by, e.g., resin.

A hole portion 29, which is illustrated in FIG. 8, is a hole for arrangement of an illumination optical system including, e.g., the light guide bundle and an illumination lens. Also, here, an example of a configuration in which the image pickup unit 30 is insert-molded in the distal end frame body 21 is indicated; however, like the image pickup unit 30, for example, an electronic module for illumination system, the electronic module including, e.g., a light source such as an LED, may be insert-molded in the distal end frame body 21.

Also, a plurality of hole portions 29 may be provided in the distal end frame body 21 and some of the plurality of hole portions 29 may be used for purposes other than the illuminating optical system, for example, for air/water feeding, a suction mechanism or a forceps hole for treatment.

Figure 9:
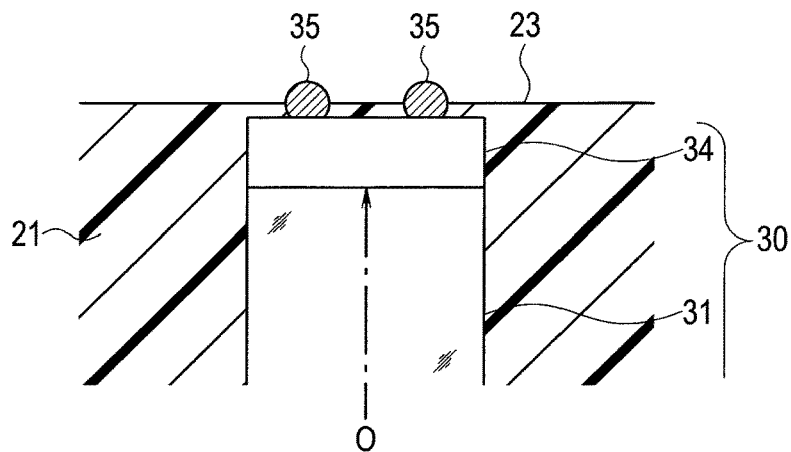
FIG. 9 is a partial cross-sectional view illustrating an example in which electrodes of the image pickup unit insert-molded in a distal end frame are exposed according to the embodiment of the present invention.

The configuration in which the electrodes 35 of the image pickup unit 30 are exposed from the one surface 23 of the distal end frame body 21 is provided by the image pickup unit 30 being insert-molded in the distal end frame body 21 in such a manner that the electrodes 35 partly project from the one surface 23 and are thus exposed as illustrated in FIG. 9.

Figure 10:
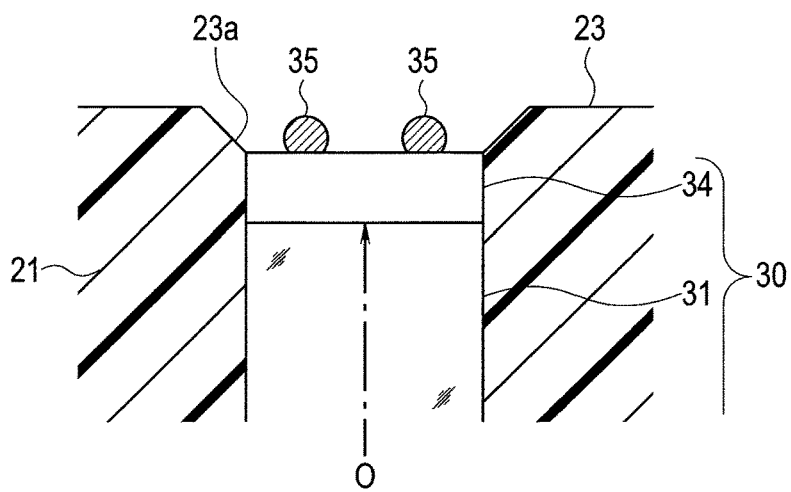
FIG. 10 is a partial cross-sectional view illustrating another example in which electrodes of the image pickup unit insert-molded in a distal end frame are exposed according to the embodiment of the present invention.

Also, the configuration in which the electrodes 35 of the image pickup unit 30 are exposed from the one surface 23 of the distal end frame body 21 may be provided by the image pickup unit 30 being insert-molded in the distal end frame body 21 in such a manner that a recessed step portion 23a that makes the entire back surface of the image sensor 34 of the image pickup unit 30 be exposed is formed on one surface as illustrated in FIG. 10.

Figure 11:
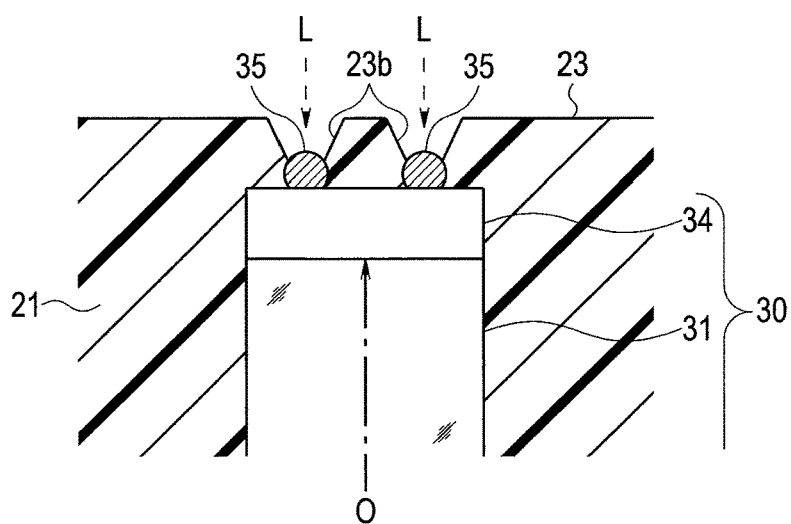
FIG. 11 is a partial cross-sectional view illustrating a configuration in which electrodes of the image pickup unit are exposed by a distal end frame being processed via, e.g., laser or grinding according to the embodiment of the present invention.

Furthermore, the configuration in which the electrodes 35 of the image pickup unit 30 are exposed from the one surface 23 of the distal end frame body 21 may be provided by the image pickup unit 30 being insert-molded in the distal end frame body 21 in such a manner that the electrodes 35 are embedded and then recess portions 23b being formed by shaving off resin on the one surface 23 side via, e.g., laser processing or grinding processing to make the electrodes 35 be exposed as illustrated in FIG. 11.

Figure 12:
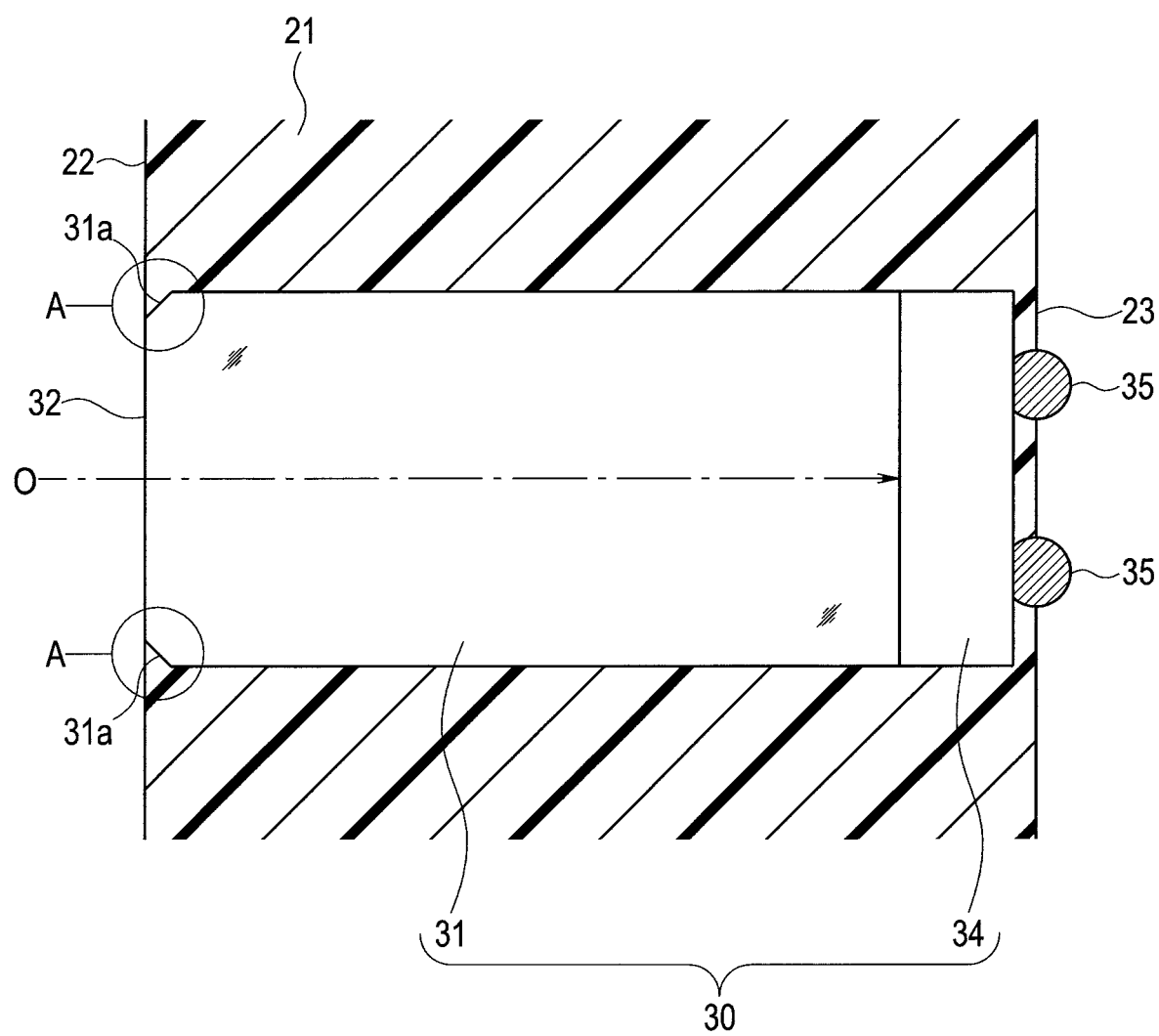
FIG. 12 is a partial cross-sectional view illustrating an image pickup unit insert-molded in a distal end frame according to the embodiment of the present invention.

Furthermore, as illustrated in FIG. 12, a tapered surface 31a may be provided at an optical system 31 of an image pickup unit 30, the optical system 31 being exposed at a distal end surface 22 of a distal end frame body 21 and the resin of the distal end frame body 21 may be charged in a cut part to cover the tapered surface 31a.

With such a configuration as above, the image pickup unit 30 is prevented from being displaced to the subject side or dropping off, by the optical system 31 being held by the resin of the distal end frame body 21 acting as a stopper.

The distal end unit 20 of the endoscope 1 of the present embodiment configured as described above has a structure in which the image pickup unit 30 is integrally mounted in the distal end frame body 21 via insert molding.

Then, the distal end unit 20 of the endoscope 1 has a configuration in which the image pickup unit 30 is insert-molded in the distal end frame body 21 in such a manner that the optical system 31 and the back-surface electrodes 35 of the image pickup unit 30 are exposed to enable easy electric connection of the signal wires 47 in the image pickup cable 48 to the electrodes 35 of the image pickup unit 30.

Consequently, the distal end unit 20 of the endoscope 1 enables reduction in manufacturing cost through facilitation of assembly by the signal wires 47 of the image pickup cable 48 being connected, via, e.g., soldering, to the electrodes 35 of the image pickup unit 30 exposed at the one surface 23 of the distal end frame body 21.

Also, the signal wires 47 of the image pickup cable 48 are individually connected to the electrodes 35 of the image pickup unit 30, enabling stable electric connection and yield enhancement.

According to the above description, the distal end unit 20 of the endoscope 1 of the present embodiment enables stable electric connection of the insert-molded image pickup unit 30 and thus enables yield enhancement and manufacturing cost reduction.

First Modification

Figure 13:
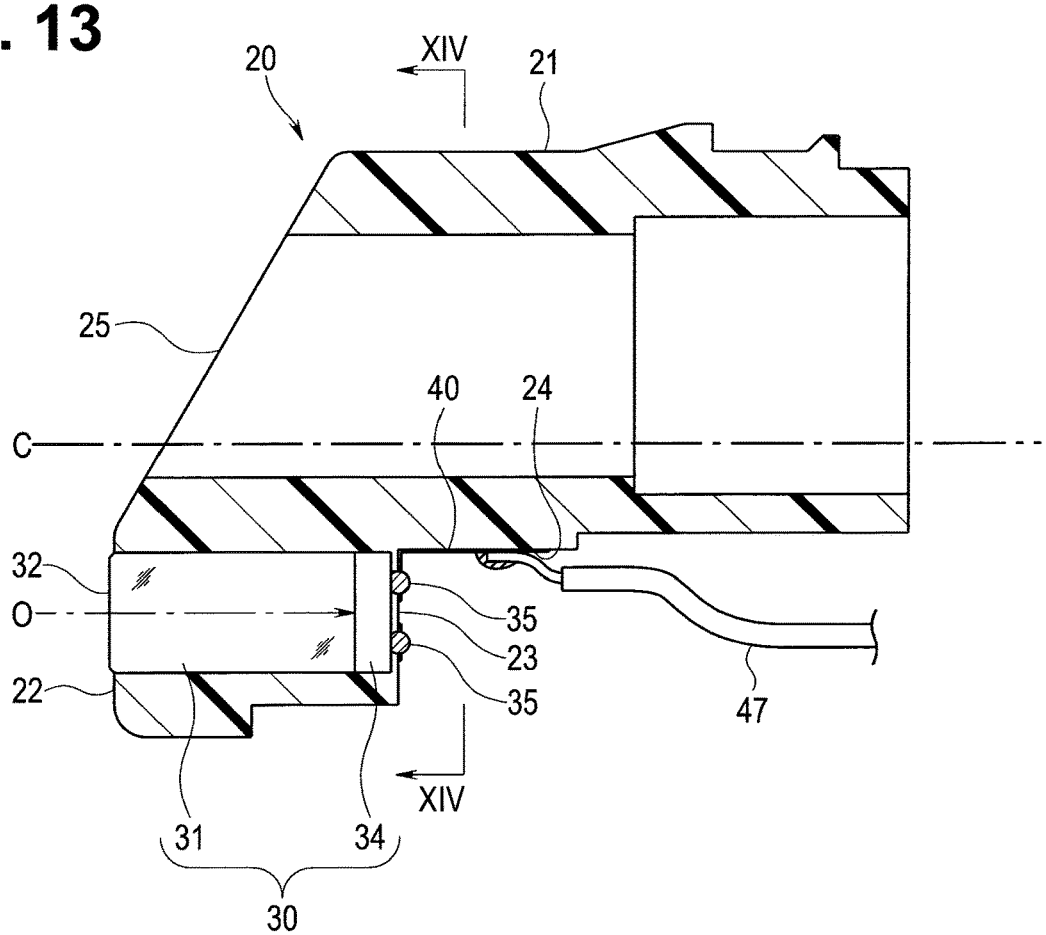
FIG. 13 is a cross-sectional view illustrating a configuration of a distal end unit of a molded interconnect device with conductive patterns formed on a surface of a distal end frame according to a first modification of the embodiment of the present invention.
Figure 14:
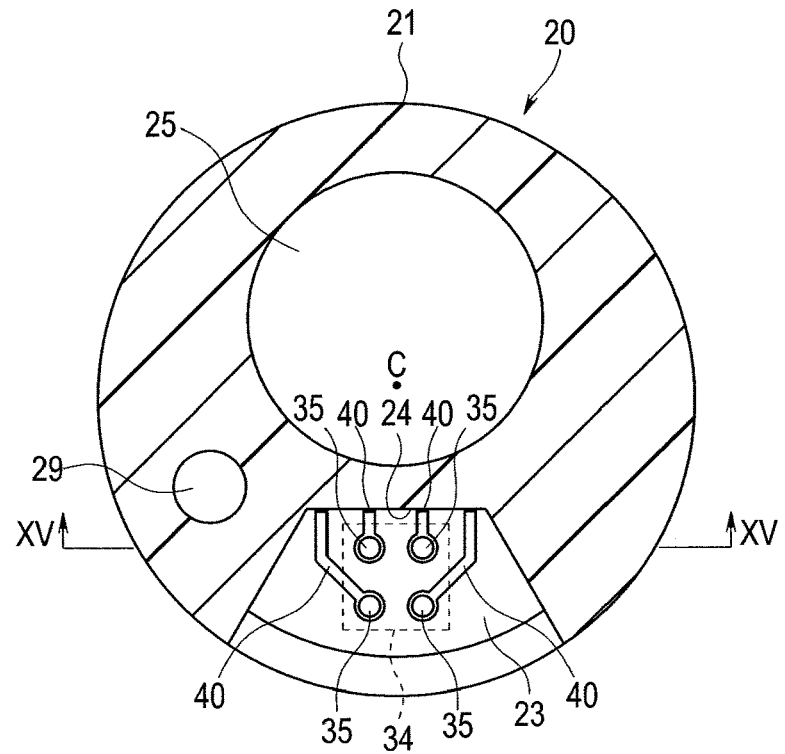
FIG. 14 is a cross-sectional view illustrating the configuration of the distal end unit along line XIV-XIV in FIG. 13 according to the first modification of the embodiment of the present invention.
Figure 15:
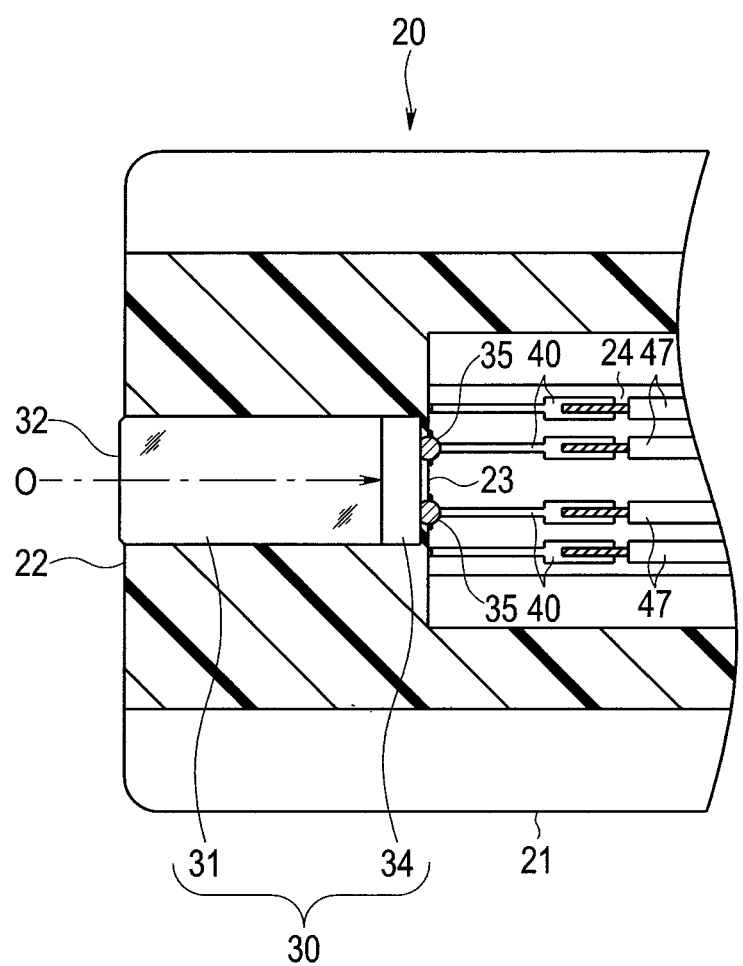
FIG. 15 is a cross-sectional view illustrating the configuration of the distal end unit along line XV-XV in FIG. 14 according to the first modification of the embodiment of the present invention.

As illustrated in FIGS. 13 to 15, the distal end frame body 21 may be a molded interconnect device (MID), conductive patterns 40 of wirings and electrodes being formed on one surface 23, which is a back surface located inside a distal end portion 6, and an inner surface 24, which is a side surface connected to the one surface 23, via, e.g., laser processing and metal plating or masking and metal plating.

The conductive patterns 40 configuring the wirings and the electrodes are electrically connected to the electrodes 35 of the image pickup unit 30 and are formed on the one surface 23 and the inner surface 24 of the distal end frame body 21.

Signal wires 47 of an image pickup cable 48 are electrically connected to the plurality of, here, four conductive patterns 40 formed on the inner surface 24 of the distal end frame body 21, via, e.g., soldering.

As described above, use of a molded interconnect device (MID) made of resin as the distal end frame body 21 enables stable electric connection between the insert-molded image pickup unit 30 and the signal wires 47 of the image pickup cable 48 via the conductive patterns 40 even though the distal end frame body 21 has a complex shape.

Furthermore, the distal end unit 20 of the molded interconnect device (MID) requires no wiring substrate or the like and also requires no step of assembling such a substrate, enabling structure simplification and cost reduction. The distal end frame body 21 has no required component precision for electric connection between the insert-molded image pickup unit 30 and the wiring substrate or the like, enabling assemblability enhancement and downsizing.

The distal end unit 20 can eliminate a metal frame or the like to the extent possible, enabling downsizing (reduction in diameter and reduction in length of a rigid part) of the distal end portion 6 of the endoscope 1.

Also, the distal end unit 20 has a configuration in which the signal wires 47 of the image pickup cable 48 are electrically connected to the conductive patterns 40 on the one surface 23 and the inner surface 24 located inside the distal end portion 6, enabling easy electrical connection of core wires and shields. For example, it is possible to form conductive patterns 40 on an area that is larger than the image pickup unit 30 and connect signal wires 47 to the conductive patterns 40.

In the distal end frame body 21, conductive patterns (not illustrated) may further be formed on surfaces around the image pickup unit 30, the electrodes 35, or the like, thus providing a shielding effect.

Figure 16:
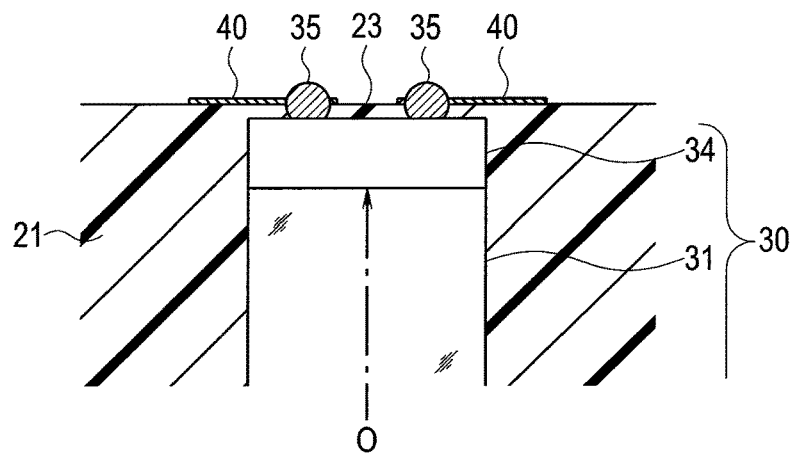
FIG. 16 is a partial cross-sectional view illustrating an example in which electrodes of an image pickup unit insert-molded in a distal end frame are exposed and illustrating a configuration of the distal end unit of the molded interconnect device with conductive patterns formed, according to the first modification of the embodiment of the present invention.

As illustrated in FIG. 16, in the case of a form in which the electrodes 35 of the image pickup unit 30 partly project from the one surface 23 and are thus exposed, a plurality of conductive patterns 40 electrically connected to the respective electrodes 35 are formed on the one surface 23 and the inner surface 24 of the distal end frame body 21.

Figure 17:
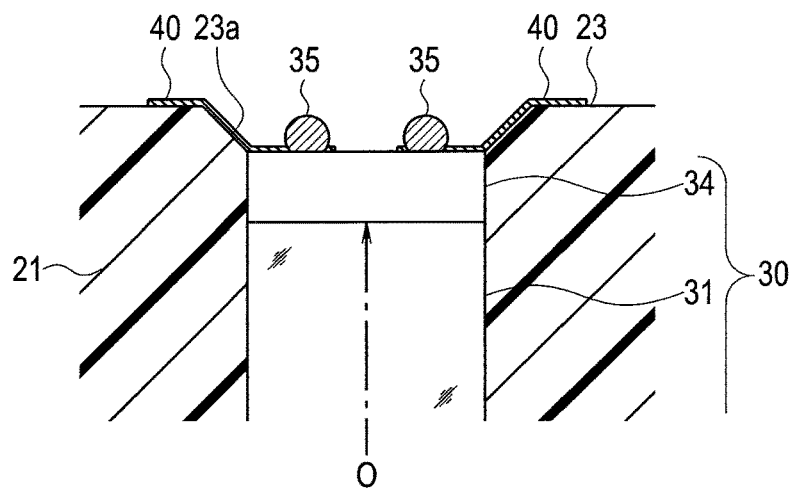
FIG. 17 is a partial cross-sectional view illustrating another example in electrodes of an image pickup unit insert-molded in a distal end frame are exposed and illustrating a configuration of the distal end unit of the molded interconnect device with conductive patterns formed, according to the first modification of the embodiment of the present invention.

Also, as illustrated in FIG. 17, in the case of a form in which an entire back surface of an image sensor 34 of an image pickup unit 30 is exposed, a plurality of conductive patterns 40 electrically connected to the respective electrodes 35 are formed on the back surface of the image sensor 34 and on a part from a surface of a step portion 23a to one surface 23 and an inner surface 24 of the distal end frame body 21.

Figure 18:
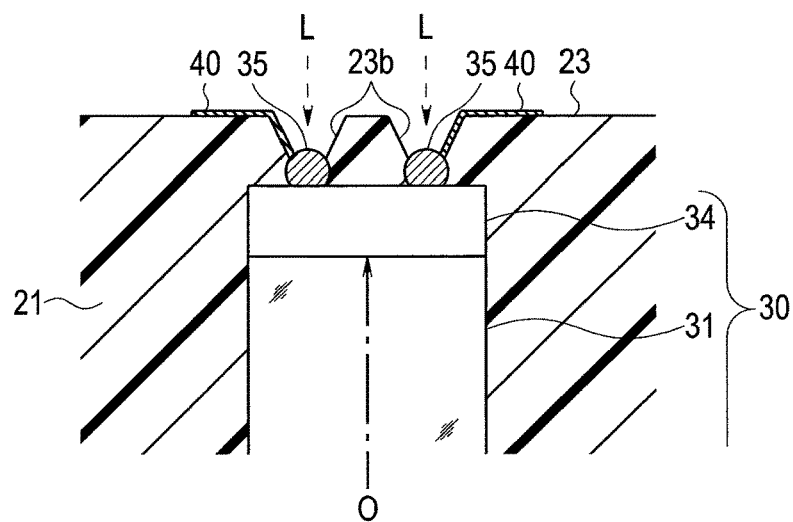
FIG. 18 is a partial cross-sectional view illustrating a configuration of the distal end unit of the molded interconnect device in which electrodes of the image pickup unit are exposed by a distal end frame being processed via, e.g., laser or grinding and conductive patterns are formed, according to the first modification of the embodiment of the present invention.

Furthermore, as illustrated in FIG. 18, in the case of a form in which electrodes 35 of an image sensor 34 are exposed by shaving off resin on the one surface 23 side via, e.g., laser processing or grinding processing, a plurality of conductive patterns 40 electrically connected to the respective electrodes 35 are formed from surfaces of recess portions 23b formed in a distal end frame body 21 via, e.g., laser processing or grinding processing to the one surface 23 and an inner surface 24.

Also, an electronic component such as a capacitor (not illustrated) for stably driving the image sensor 34 of the image pickup unit 30 can be mounted in the vicinity of the image sensor 34 via a conductive pattern 40.

Second Modification

Figure 19:
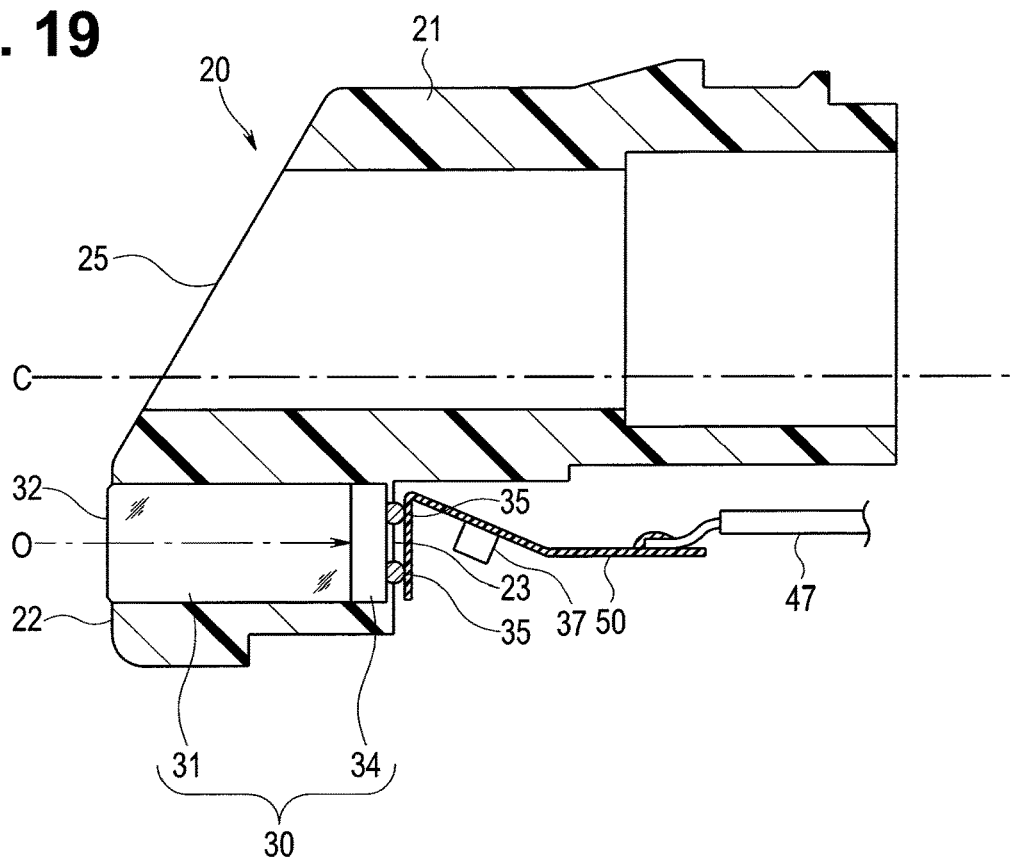
FIG. 19 is a cross-sectional view illustrating a configuration of a distal end unit in which a flexible printed circuit board is connected to an image pickup unit, according to a second modification of the embodiment of the present invention.

As illustrated in FIG. 19, electrodes 35 of an image pickup unit 30 of a distal end unit 20 and signal wires 47 of an image pickup cable 48 may be electrically connected via a flexible printed circuit board (FPC) 50.

Consequently, a simple configuration in which electrodes exposed on the FPC 50 that is electrically connected to the image pickup unit 30 and that extends from one surface 23 of a distal end frame body 21 to the proximal end side and the signal wires 47 of the image pickup cable 48 can be connected via, e.g., soldering is provided.

It is also possible that an electronic component such as a capacitor 37 for stably driving an image sensor 34 of the image pickup unit 30 is provided on a part of the FPC 50, the part being in the vicinity of the image sensor 34.

The substrate interposed between the image pickup unit 30 and the signal wires 47 of the image pickup cable 48 is not limited to the FPC 50 but may be any of various substrates such as a ceramic substrate, a glass epoxy substrate, a silicon substrate and a glass substrate.

Third Modification

Figure 20:
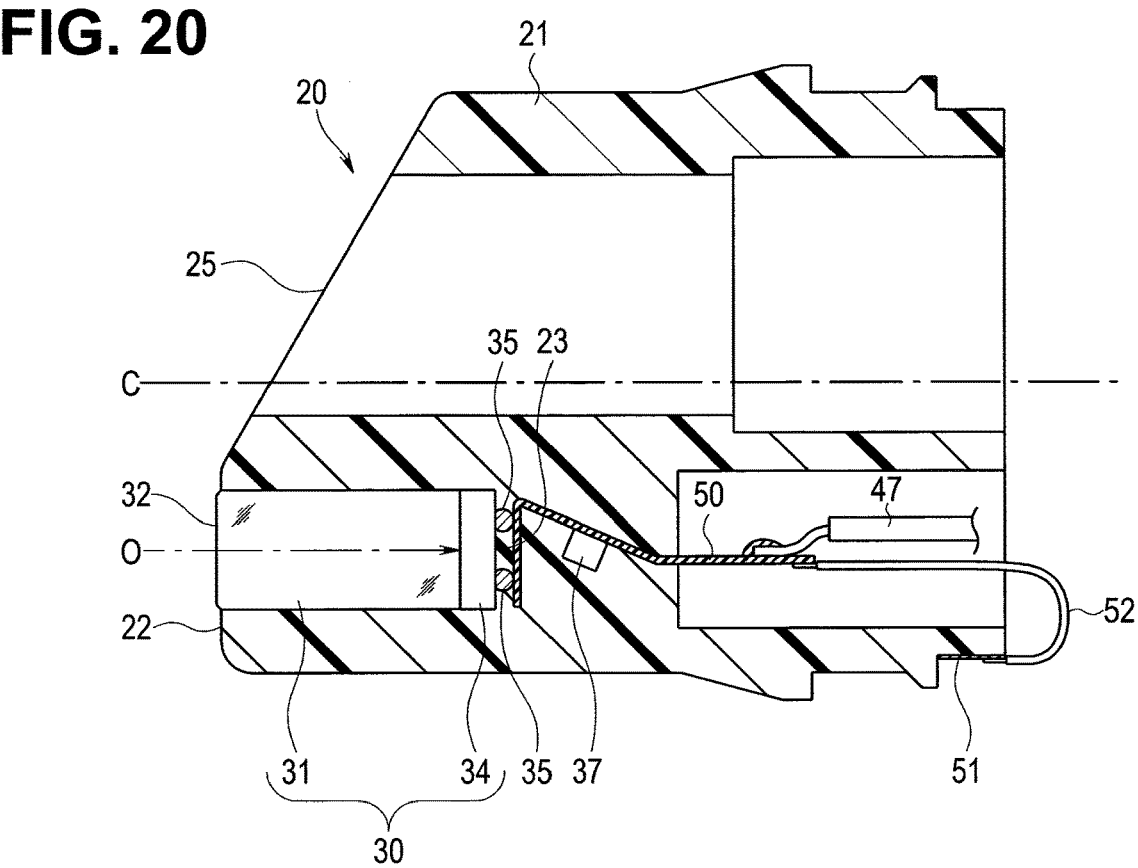
FIG. 20 is a cross-sectional view illustrating a configuration of a distal end unit in which a flexible printed circuit board is connected to an image pickup unit in advance and is insert-molded in a distal end frame, according to a third modification of the embodiment of the present invention.

As illustrated in FIG. 20, a flexible printed circuit board (FPC) 50 may be formed integrally with a distal end frame body 21 made of resin, via insert molding by the FPC 50 being connected to electrodes 35 of an image pickup unit 30 in advance and loading the FPC 50 in a non-illustrated mold together with the image pickup unit 30.

Here, also a simple configuration in which electrodes exposed on the FPC 50 provided in such a manner as to extend from one surface 23 of the distal end frame body 21 to the proximal end side and signal wires 47 of an image pickup cable 48 can be connected via, e.g., soldering is provided.

Furthermore, a GND electrode 51 formed on an outer peripheral portion of the distal end frame body 21 and the FPC 50 may be electrically connected via a GND wire 52. Consequently, a larger GND area can be secured, enabling an image sensor 34 to be stably driven.

Also, instead of the GND electrode 51 and the FPC 50 being connected, the GND electrode 51, and a distalmost bending piece 41, bending operation wires, a cable integration sheath, etc., may be electrically connected as a countermeasure for static electricity of the image pickup unit 30.

The distal end frame body 21 may be a molded interconnect device (MID) made of resin, the GND electrode 51 being formed on a surface of the MID.

Also, instead of the FPC 50, any of various substrates such as a ceramic substrate, a glass epoxy substrate, a silicon substrate and a glass substrate may be used.

Fourth Modification

Figure 21:
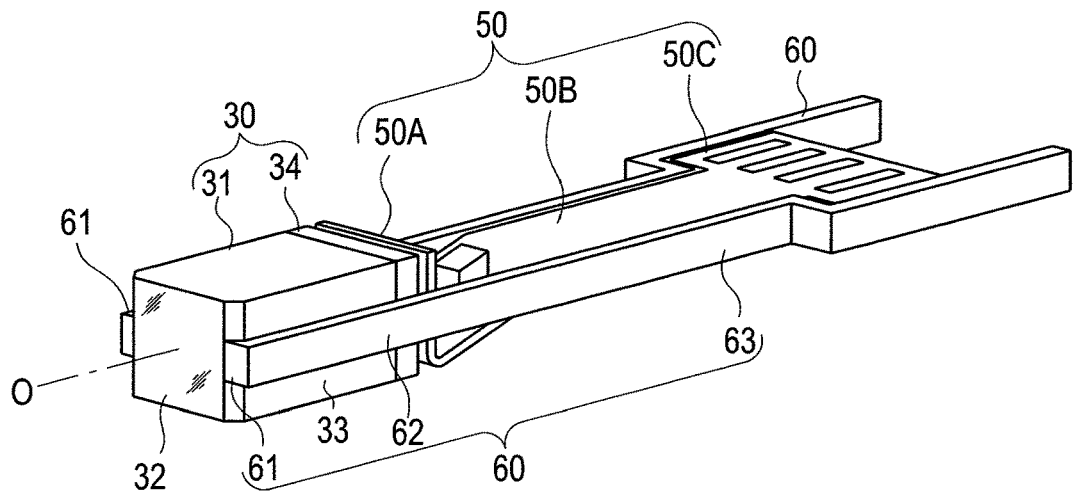
FIG. 21 is a perspective view illustrating a configuration of a holding member that holds an image pickup unit to which a flexible printed circuit board is connected, according to a fourth modification of the embodiment of the present invention.
Figure 22:
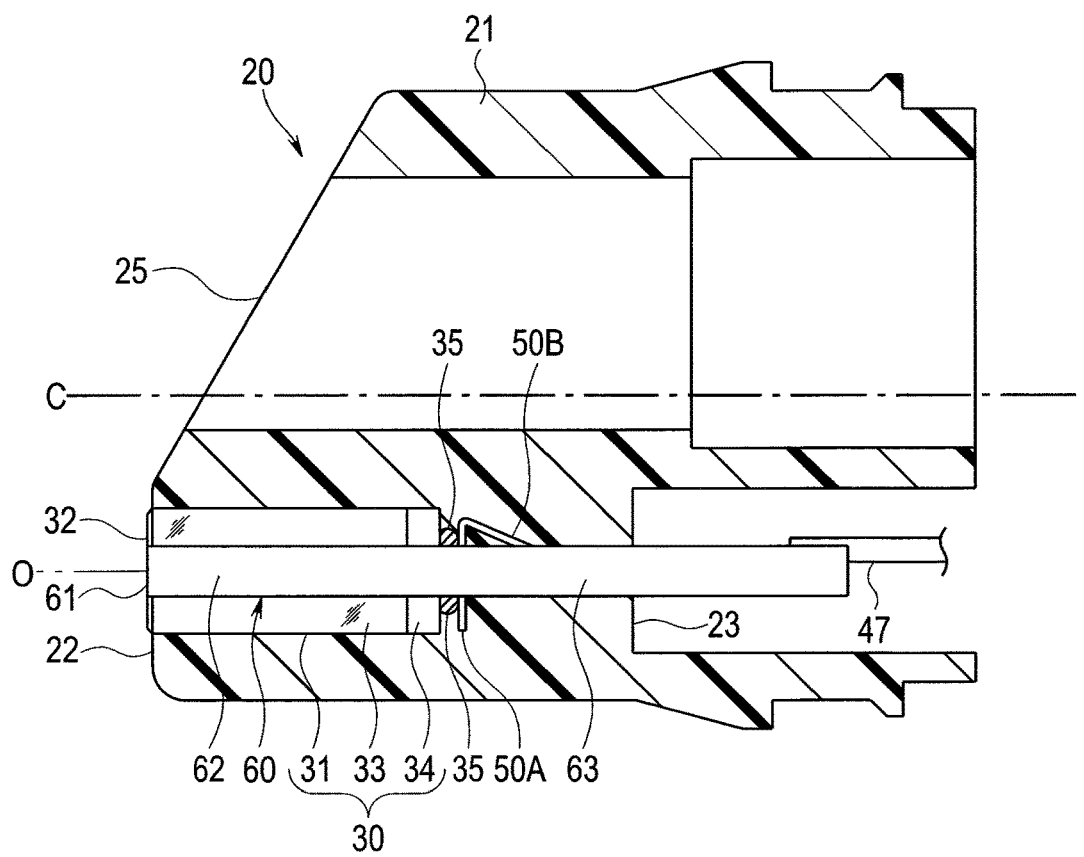
FIG. 22 is a cross-sectional view illustrating a configuration of a distal end unit in which an image pickup unit to which a flexible printed circuit board is connected is insert-molded in a distal end frame together with a holding member, according to the fourth modification of the embodiment of the present invention.

As illustrated in FIGS. 21 and 22, a holding member 60 configured to hold an image pickup unit 30 and a flexible printed circuit board (FPC) 50 electrically connected to the image pickup unit 30 may be provided, and integrally molded in a distal end frame body 21 made of resin via insert molding by loading the holding member 60 together with the image pickup unit 30 and the FPC 50 in a non-illustrated mold.

The holding member 60 includes two arm members. A drop-off preventing claw portion 61 configured to hold an optical system 31 of the image pickup unit 30 is provided at a distal end part of each arm member.

Furthermore, each arm member includes a fixed portion 62 fixed to a side surface 33 of the image pickup unit 30 and a lead portion 63 extending from the fixed portion 62 to the proximal end side. The two fixed portions 62 hold the image pickup unit 30 by sandwiching the two side surfaces 33 facing each other. Alternatively, each fixed portion 62 may be fixed to the relevant side surface 33 of the image pickup unit via an adhesive.

If the image pickup unit 30 can be held by a fixed portion 62 being bonded to a side surface 33, there is no need to necessarily provide two arm members. The necessary function can be fulfilled by provision of at least one arm member. A shape of the fixed portions 62 may be a shape other than the illustrated plate-like shape, for example, a shape that allows grasping the image pickup unit 30.

In the FPC 50, a first connection portion 50A is provided on the distal end side, a second connection portion 50C is provided on the proximal end side and a relay portion 50B is provided between the two connection portions. On the first connection portion 50A, a connection and electrically connected to electrodes 35 of an image sensor 34 is formed, and on the second connection portion 50C, a connection land on which electronic components (e.g., cable wires, a capacitor and a semiconductor element) are connected via soldering is formed. On the relay portion 50B, a wiring pattern electrically connecting the connection lands is formed.

The holding member 60 being fixed to the image pickup unit 30 and the FPC 50 to be insert-molded, in advance facilitates positioning in the mold. A distal end portion 6 manufactured by an image pickup unit 30 being integrally molded in a distal end frame body 21 has the following structural characteristics. A surface that is an entrance surface 32 of an optical system 31 of the image pickup unit 30 is exposed from a distal end surface 22 of the distal end frame body 21.

An end surface 61 on the distal end side of each arm member is exposed from the distal end surface 22 of the distal end frame body 21. Furthermore, a fixed portion 62 of each arm member is located inside the distal end frame body 21 but a lead portion 63 of each arm member extends to the proximal end side and projects from one surface 23 of the distal end frame body 21 and is thus exposed to the outside of the distal end frame body 21.

Each exposed lead portion 63 may be connected to a GND of the endoscope via some kind of conductive member. A first connection portion of an FPC 50 is located inside the distal end frame body 21, a relay portion 50B of the FPC 50 extends to the proximal end side and projects from the one surface 23 of the distal end frame body 21, and a second connection portion is exposed to the outside of the distal end frame body 21. The FPC 50 needs at least the first connection portion to be located inside the distal end frame body 21. As for the relay portion 50B, a part that needs to be located inside the distal end frame body 21 is located inside the distal end frame body 21 and the rest part is exposed to the outside of the distal end frame body 21.

Also, a material of the holding member 60 can arbitrarily be selected, and the holding member 60 is formed by, for example, a conductive member, enabling the holding member 60 to form a pathway for releasing current such as static electricity or radio-frequency radiation applied to the distal end portion 6 of the insertion portion 2 of the endoscope 1. Also, where a pathway for releasing current such as static electricity or radio-frequency radiation is formed by the holding member 60, a distance between the image sensor 34 and the holding member 60 is made to be large only in the vicinity of the image sensor 34, which makes it further difficult to apply current such as static electricity or radio-frequency radiation to the image sensor 34. Consequently, it is possible to provide an endoscope with high resistance to static electricity and radio-frequency radiation.

Fifth Modification

The above-described configuration of the image pickup unit 30 inserted in the above-described distal end frame body 21 has a structure in which the entrance surface 32 of the optical system 31, into which light of a subject image along the image pickup optical axis O enters, the image pickup optical axis O being substantially parallel to the longitudinal axis C of the distal end frame body 21, is in plane with the distal end surface 22 of the distal end frame body 21 provided in the distal end portion 6 of the endoscope 1 or projects relative to the distal end surface 22 of the distal end frame body 21, and indicates an example of a configuration of what is called a front-viewing endoscope in which light of a subject image along the image pickup optical axis O directly enters the image sensor 34. However, any of various forms of endoscope 1 described below may be employed.

Figure 23:
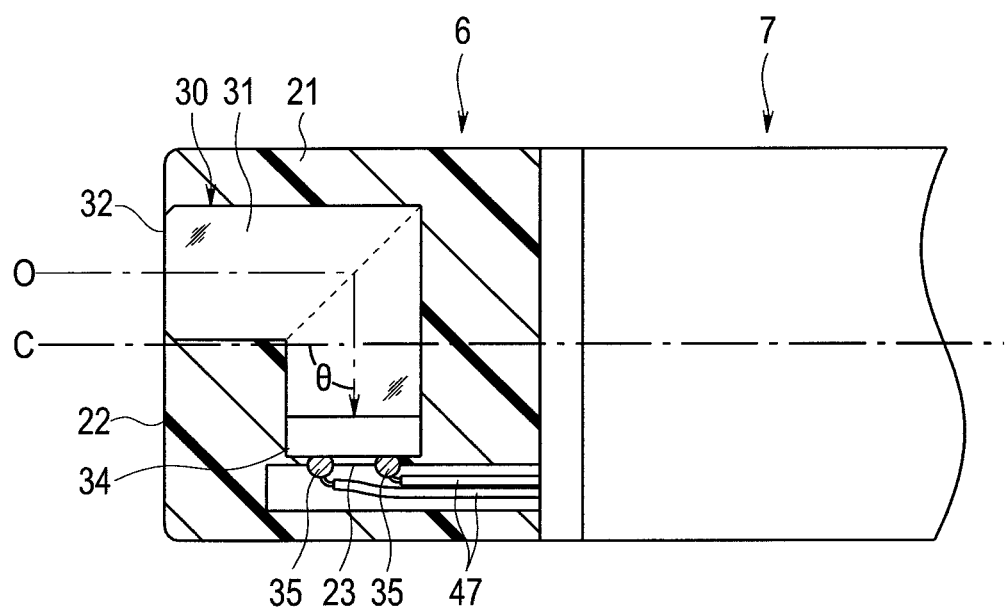
FIG. 23 is a partial cross-sectional view illustrating a configuration of a distal end part of an insertion portion in which an image pickup unit with an observation window provided in a distal end surface and an image sensor laterally mounted is insert-molded in a distal end frame, according to a fifth modification of the embodiment of the present invention.

As illustrated in FIG. 23, in an image pickup unit 30, an entrance surface 32 of an optical system 31 is disposed in plane with a distal end surface 22 of a distal end frame body 21 or projects relative to the distal end surface 22 of the distal end frame body 21 and an image sensor 34 is laterally disposed perpendicularly to the distal end surface 22. In an optical system 31 of the image pickup unit 30, an optical element such as a prism unit or a mirror (not illustrated) having a refractive surface that refracts light of a subject image along an image pickup optical axis O in a direction substantially perpendicular to a longitudinal axis C of the distal end frame body 21 (crossing angle θ between the image pickup optical axis O and the longitudinal axis C of the distal end frame body 21 ≈90 degrees) is provided.

Consequently, light entering the optical system 31 along the image pickup optical axis O enters the laterally-mounted image sensor 34 that is parallel to the longitudinal axis C. The endoscope 1 here has a form of what is called a front-view type. This configuration enables reduction in length of a rigid part.

Figure 24:
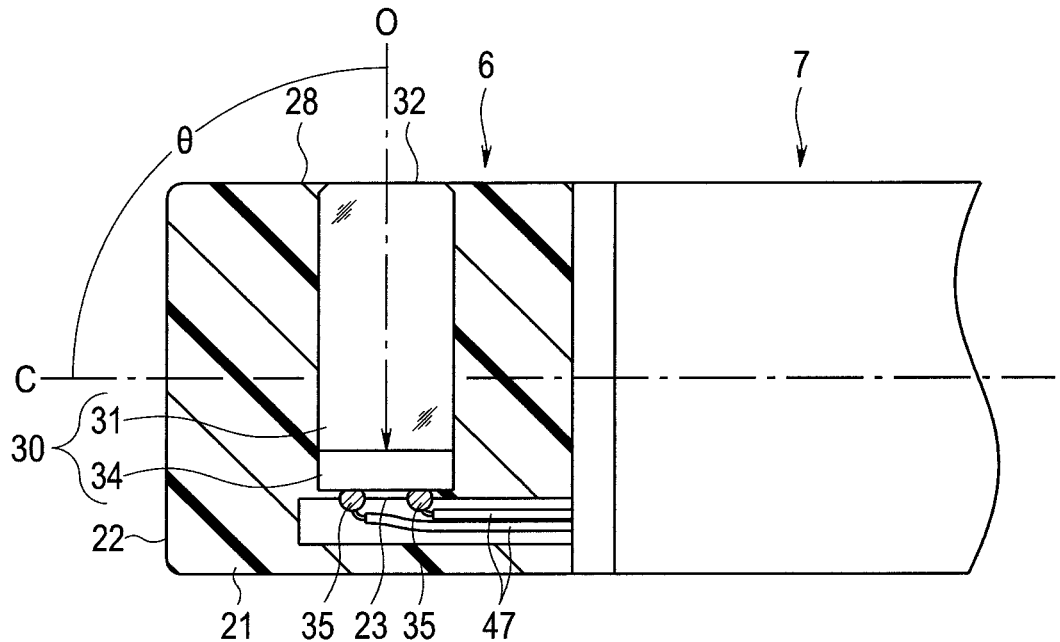
FIG. 24 is a partial cross-sectional view illustrating a configuration of a distal end part of an insertion portion in which an image pickup unit including an observation window provided in a side surface perpendicular to a distal end surface and an image sensor laterally mounted is insert-molded in a distal end frame, according to the fifth modification of the embodiment of the present invention.

As illustrated in FIG. 24, in an image pickup unit 30, an entrance surface 32 of an optical system 31 is disposed in plane with a side surface 28 substantially perpendicular to a distal end surface 22 of a distal end frame body 21 or projects relative to the side surface 28 and light of a subject image along an image pickup optical axis O substantially perpendicular to a longitudinal axis C of a distal end frame body 21 (crossing angle θ between the image pickup optical axis O and the longitudinal axis C of the distal end frame body 21 ≈90 degrees) directly enters a laterally-mounted image sensor 34 that is parallel to the longitudinal axis C.

The endoscope 1 here has a form of what is called a side-view type. This configuration enables observation in a side surface direction of the endoscope and thus enables observation of, e.g., the inside of a narrow tubular body cavity with minimum bending of the endoscope.

Figure 25:
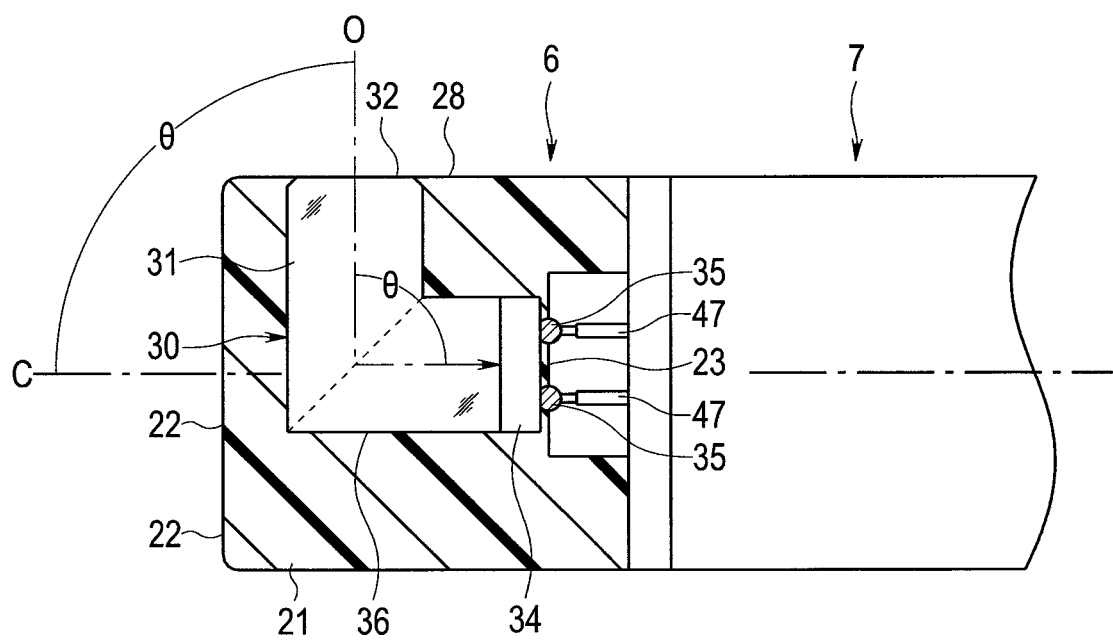
FIG. 25 is a partial cross-sectional view illustrating a configuration of a distal end part of an insertion portion in which an image pickup unit including an observation window provided in a side surface perpendicular to a distal end surface and an image sensor longitudinally mounted is insert-molded in a distal end frame, according to the fifth modification of the embodiment of the present invention.

As illustrated in FIG. 25, in an image pickup unit 30, an entrance surface 32 of an optical system 31 is disposed in plane with the side surface 28 of a distal end frame body 21 or projects relative to the side surface 28, an optical element such as a prism unit or a mirror (not illustrated) including a refractive surface that refracts light of a subject image along an image pickup optical axis O in a direction substantially perpendicular to a longitudinal axis C of a distal end frame body 21 (crossing angle θ between the image pickup optical axis O and the longitudinal axis C of the distal end frame body 21 ≈90 degrees) is provided, and an image sensor 34 is longitudinally disposed perpendicularly to the longitudinal axis C.

The endoscope 1 here also has a form of what is called a side-view type. This configuration enables observation in a side surface direction of the endoscope and thus enables observation of, e.g., the inside of a narrow tubular body cavity with minimum bending of the endoscope. Furthermore, this configuration enables reduction in diameter of the endoscope.

Figure 26:
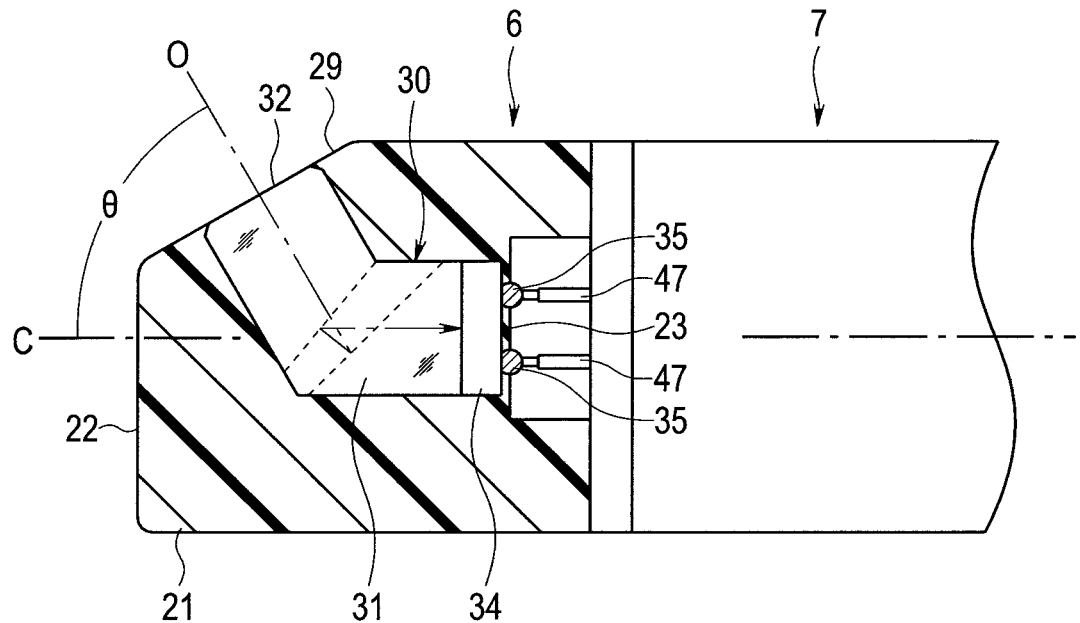
FIG. 26 is a partial cross-sectional view illustrating a configuration of a distal end part of an insertion portion in which an image pickup unit including an observation window provided in an inclined surface forming a predetermined angle with a distal end surface and an image sensor longitudinally mounted is insert-molded in a distal end frame, according to the fifth modification of the embodiment of the present invention.

As illustrated in FIG. 26, in an image pickup unit 30, an entrance surface 32 of an optical system 31 is disposed in such a manner as to be in plane with an inclined surface 29 having a predetermined angle relative to a distal end surface 22 of a distal end frame body 21 or project relative to the inclined surface 29.

In the optical system 31 of the image pickup unit 30, an optical element such as a prism unit or a mirror (not illustrated) configured to refract light of a subject image along an image pickup optical axis O at a predetermined angle θ of less than 90 degrees relative to a longitudinal axis C of the distal end frame body 21 (crossing angle θ between the image pickup optical axis O and the longitudinal axis C of the distal end frame body 21 <90 degrees) is provided.

In the image pickup unit 30 here, an image sensor 34 is longitudinally disposed in parallel with the distal end surface 22 of the distal end frame body 21 and perpendicularly to the longitudinal axis C. In other words, the endoscope 1 has a form of what is called an oblique-view type. This configuration enables observation in an oblique direction with minimum bending of the endoscope.

Figure 27:
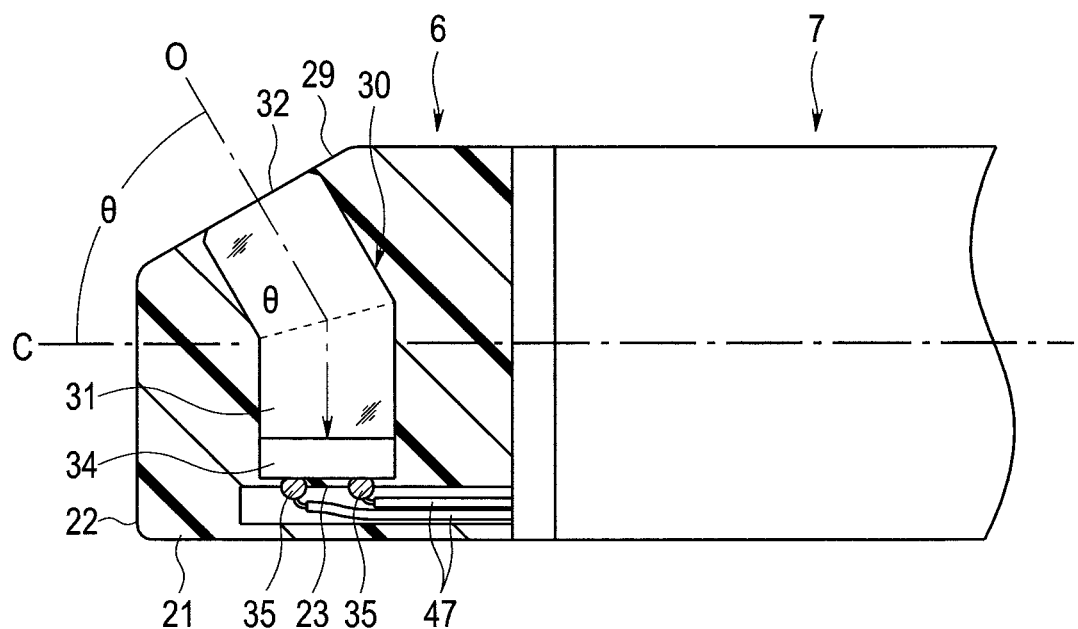
FIG. 27 is a partial cross-sectional view illustrating a configuration of a distal end part of an insertion portion in which an image pickup unit including an observation window provided in an inclined surface forming a predetermined angle with a distal end surface and an image sensor laterally mounted is insert-molded in a distal end frame, according to the fifth modification of the embodiment of the present invention.

As illustrated in FIG. 27, in an image pickup unit 30, an entrance surface 32 of an optical system 31 is disposed in such a manner as to be in plane with the inclined surface 29 having a predetermined angle relative to a distal end surface 22 of a distal end frame body 21 or project relative to the inclined surface 29.

In the optical system 31 of the image pickup unit 30, an optical element such as a prism unit or a mirror (not illustrated) configured to refract light of a subject image along an image pickup optical axis O at a predetermined angle θ of less than 90 degrees relative to a longitudinal axis C of the distal end frame body 21 (crossing angle θ between the image pickup optical axis O and the longitudinal axis C of the distal end frame body 21 <90 degrees) is provided.

In the image pickup unit 30 here, an image sensor 34 is laterally disposed substantially perpendicularly to a distal end surface 22 of the distal end frame body 21. In other words, the endoscope 1 also has a form of what is called an oblique-view type. This configuration enables observation in an oblique direction with minimum bending of the endoscope. Furthermore, the configuration can be provided using a simple optical element such as a prism unit or a mirror (not illustrated), enabling cost reduction.

Figure 28:
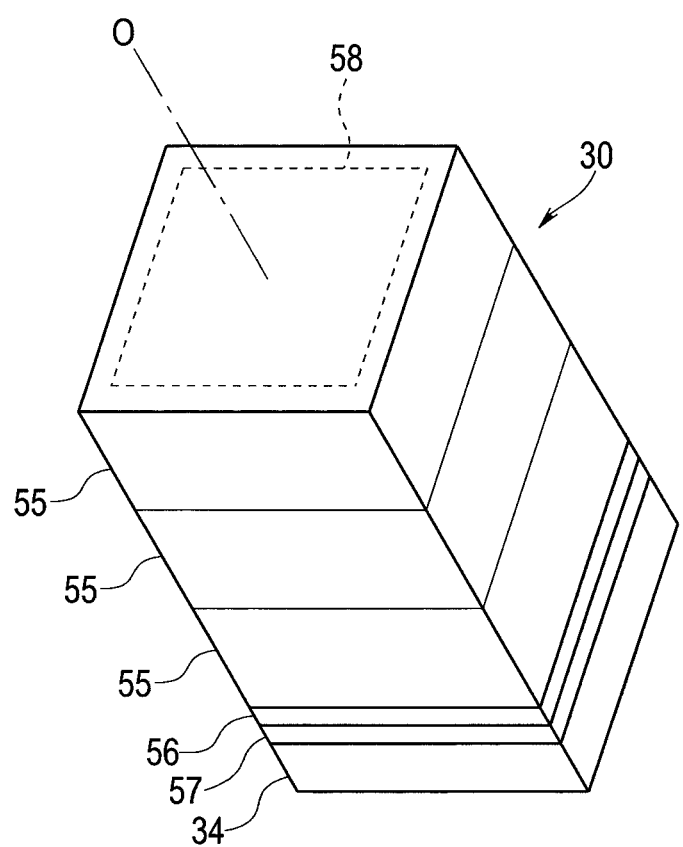
FIG. 28 is a perspective view illustrating a configuration of an image pickup unit including an image pickup lens unit fabricated using a wafer-level optics technique, according to the fifth modification of the embodiment of the present invention.

In the present embodiment, the image pickup unit 30 provided in the distal end frame body 21 as one of functional components is configured, for example, by a CSP (chip size package) with an image pickup lens unit 55, a cover glass 56 and an image sensor 34 integrally packaged as illustrated in FIG. 28, the image pickup lens unit 55 being formed of a lens stack body fabricated using a wafer-level optics technique, the image sensor 34 being an image pickup device and being attached to the cover glass 56 via a bonding layer 57.

In such an image pickup unit 30, the image pickup lens unit 55 is manufactured by, e.g., fabricating a plurality of lens wafers each including a lens formed on a base material such as a glass substrate and stacking and dicing these lens wafers.

Therefore, the image pickup lens unit 55 of the present embodiment is a lens unit having a rectangular shape in plan view and includes no lens frame. Also, the image sensor 34 is formed in such a manner as to have a rectangular shape in plan view, by, e.g., dicing, and thus, the image pickup unit 30 of the present embodiment has a substantially rectangular parallelepiped shape as a whole.

Furthermore, the image pickup lens unit 55 includes an effective image pickup area 58, which is an optically effective area indicated by dashed lines. Light forming an optical image enters the effective image pickup area 58.

The configuration of the electronic module may include, e.g., a passive element (e.g., a resistance or a coil), an active element (e.g., a transistor or an IC), an light-emitting apparatus (e.g., an LED, a laser diode or a lamp), an observation/communication device (e.g., a temperature observation apparatus, a moisture observation apparatus, an in-vivo information measuring apparatus and/or a wireless transmission device) other than the image pickup unit 30.

The invention described in the above embodiment and modifications are not limited to the embodiment and modifications and various modifications are possible in a practical phase without departing from the gist of the invention. Furthermore, the above embodiment and modifications include various phases of the invention and various aspects of the invention may be extracted by arbitrary combinations of a plurality of elements disclosed.

For example, even where some elements are deleted from all the elements indicated in the embodiment and modifications, a configuration with the elements deleted can be extracted as an aspect of the invention if such a configuration can solve the above-stated problem and provide the above-described effects.

(Supplement)

A distal end unit for endoscope, the distal end unit being provided in a distal end portion of an insertion portion, the distal end unit including:
an image pickup unit including at least an optical system and an image sensor;
a flexible substrate including a first connection portion electrically connected to an electrode of the image sensor and a second connection portion to which an electronic component is connected;
arm members arranged on (bonded to) respective side surfaces of the image pickup unit, the side surfaces facing each other; and
a distal end frame body made of resin, on which the image pickup unit, the flexible substrate and the arm member are integrally mounted via insert molding, wherein
only a surface of the optical system of the image pickup unit is exposed from a distal end surface of the distal end frame body,
an end surface on a distal end side of each arm member is exposed from the distal end surface of the distal end frame body, a fixed portion of each arm member, the fixed portion being fixed (bonded) to the image pickup unit, is provided (inserted) in the distal end frame body, and a lead portion on a proximal end of each arm member is exposed from a surface located inside the distal end frame body, and
at least the first connection portion of the flexible substrate is provided (inserted) in the distal end frame body and the second connection portion of the flexible substrate is exposed.

Although in the above embodiment, a pair of holding members is indicated as an example of the arm members, it is only necessary that at least one holding member is provided. Also, in the above flexible substrate, a connection land electrically connected to the electrode of the image sensor is arranged on the first connection portion and a connection land to which, e.g., a capacitor and a lead wire are electrically connected is arranged on the second connection portion.

Furthermore, each arm member is partially splittable and includes a fixed portion (part to which the image pickup unit is fixed by bonding or holding) and a lead portion (exposed part extending in a proximal end direction) in addition to the end surface.

What is claimed is:

1. A distal end unit for use with an endoscope, the distal end unit comprising:
   an electronic module including an optical system and an electrode;
   a substrate comprising:
      a first connection portion including a first connection land electrically connected to the electrode; and
      a second connection portion provided proximally relative to the first connection portion, the second connection portion including a second connection land on which an electronic component is mounted;
   a holding frame holding the electronic module and the substrate, the holding frame comprising:
      an arm member; and
      a claw disposed at a distal end of the arm member, the claw configured to hold the optical system; and
   a distal end frame body, on which the electronic module, the substrate and the holding frame are mounted;
   wherein the second connection portion extends proximally in a longitudinal axis direction of the distal end frame body.

2. The distal end unit according to claim 1, wherein an entrance surface of the optical system is disposed in plane with an outer surface of the distal end frame body or the entrance surface of the optical system projects from the outer surface of the distal end frame body.

3. The distal end unit according to claim 1, wherein the electronic module is an image pickup unit including an image sensor.

4. The distal end unit according to claim 3, wherein
   the image sensor includes a first surface and a second surface opposite to the first surface,
   the optical system is disposed on the first surface,
   the electrode is disposed on the second surface.

5. The distal end unit according to claim 1, wherein the electrode is exposed so as to at least partly project from an inner surface of the distal end frame body.

6. The distal end unit according to claim 1, wherein an end surface of the arm member is exposed at an outer surface of the distal end frame body.

7. An endoscope comprising:
   the distal end unit according to claim 1;

wherein the distal end unit is provided in a distal end portion of an insertion portion.

8. The distal end unit according to claim 1, wherein an inner surface of the holding frame is in contact with an outer surface of the substrate.

9. The distal end unit according to claim 1, wherein the arm member further comprises:
- a fixed portion disposed proximally relative to the claw, the fixed portion holding the optical system; and
- a lead portion extending proximally relative to the fixed portion.

10. The distal end unit according to claim 9, wherein
the fixed portion comprises a plurality of the fixed portions, each holding the optical system; and
the plurality of the fixed portions sandwich the optical system.

11. The distal end unit according to claim 9, further comprising an adhesive to fix the fixed portion to a side surface of the optical system.

12. The distal end unit according to claim 1, wherein the substrate further comprises a relay portion located between the first connection portion and the second connection portion, the relay portion including a wiring pattern connecting the first connection land and the second connection land.

13. The distal end unit according to claim 1, wherein the first connection portion is disposed inside the distal end frame body, the second connection land is disposed in a space formed in the distal end frame body.

14. The distal end unit according to claim 1, wherein the holding frame is formed of a conductive member.

15. The distal end unit according to claim 1, wherein the distal end frame body is made of resin, on which the electronic module, the substrate and the holding frame are integrally mounted.

16. The distal end unit according to claim 1, wherein the electronic module, the substrate and the holding frame are embedded within the distal end frame body.

17. The distal end unit according to claim 1, wherein
a tapered surface is disposed on a distal end of the optical system, and
the holding frame is in contact with the tapered surface to hold the optical system.

18. The distal end unit according to claim 1, wherein an entrance surface of the optical system is exposed at an outer surface of the distal end frame body.

* * * * *